US006620589B1

(12) United States Patent
Sem et al.

(10) Patent No.: US 6,620,589 B1
(45) Date of Patent: **\*Sep. 16, 2003**

(54) NMR-SOLVE METHOD FOR RAPID IDENTIFICATION OF BI-LIGAND DRUG CANDIDATES

(75) Inventors: Daniel S. Sem, San Diego, CA (US); Maurizio Pellecchia, San Diego, CA (US); Anna Tempczyk-Russell, San Diego, CA (US)

(73) Assignee: Traid Therapeutics, Inc., San Diego, CA (US)

( * ) Notice: Subject to any disclaimer, the term of this patent is extended or adjusted under 35 U.S.C. 154(b) by 49 days.

This patent is subject to a terminal disclaimer.

(21) Appl. No.: 09/587,584

(22) Filed: Jun. 2, 2000

Related U.S. Application Data

(63) Continuation-in-part of application No. 09/326,435, filed on Jun. 4, 1999, now Pat. No. 6,333,149.

(51) Int. Cl.$^7$ .............................................. G01N 33/53
(52) U.S. Cl. ............................ 435/7.1; 435/15; 435/16; 435/25; 435/26
(58) Field of Search ........................ 435/7.1, 15, 16, 435/25, 26

(56) References Cited

U.S. PATENT DOCUMENTS

| 5,658,739 | A |  | 8/1997 | Woods, Jr. ................... 435/7.1 |
| 5,693,515 | A |  | 12/1997 | Clark et al. ................. 435/184 |
| 5,698,401 | A |  | 12/1997 | Fesik et al. .................. 435/7.1 |
| 5,804,390 | A |  | 9/1998 | Fesik et al. .................. 435/7.1 |
| 2001/0006822 | A1 | * | 7/2001 | Sem |

FOREIGN PATENT DOCUMENTS

| WO | 97/18469 | 5/1997 |
| WO | 97/18471 | 5/1997 |
| WO | 98/48264 | 10/1998 |

OTHER PUBLICATIONS

Appelt et al., "Design of enzyme inhibitors using iterative protein crystallographic analysis," *J. Med. Chem.* 34:1925–1934 (1991).
Borman, "Advance in NMR of Macromolecules," *Chem. & Eng. News* 76:55–56 (1998).
Chen, et al., "Biased combinatorial libraries: novel ligands for the SH3 domain of phosphatidylinositol 3–kinase," *J. Am. Chem. Soc.* 115:12591–12592 (1993).
Chen et al., "Mapping of the Binding Interfaces of the Proteins of the Bacterial Phosphotransferase System, HPr and IIA$^{glc}$," *Biochemistry* 32:32–37 (1993).
Combs et al., "Protein structure–based combinatorial chemistry: discovery of non–peptide binding elements to Src SH3 domain," *J. Am. sChem. Soc.* 118:287–288 (1996).

Davis et al., "Alterations in chemical shifts and exchange broadening upon peptide boronic acid inhibitor binding to α–lytic protease," *J. Biomolecular NMR* 10:21–27 (1997).
Fejzo et al., "The Shapes strategy: an NMR–based approach for lead generation in drug discovery," *Chem. & Biol.* 6(10):755–769 (1999).
Hajduk et al., "High–throughput nuclear magnetic resonance–based screening," *J. Med. Chem.* 42(13):2315–2317 (1999).
Hajduk et al., "Discovery of Potent Nonpeptide Inhibitors of Stromelysin Using SAR by NMR," *J. Am. Chem. Soc.* 119:5818–5827 (1997).
He et al., "Design and synthesis of new leads for PKC bisubstrate inhibitors," *Bioorganic & Medicinal Chemistry Letters* 4:2845–2850 (1994).
Hrovat et al., "Backbone dynamics of oxidized and reduced *D. vulgaris* flavodoxin in solution," *J. Biomolecular NMR* 10:53–62 (1997).
Labrou et al., "Molecular modelling for the design of chimaeric biomimetic dye–ligands and their interaction with bovine heart mitochondrial malate dehydrogenase," *Biochem. J.* 315:695–703 (1996).
Labrou et al., "Oxaloacetate Decarboxylase: On the Mode of Interaction with Substrate–Mimetic Affinity Ligands," *Arch. Biochem. Biophys.* 321(1):61–70 (1995).
Labrou et al., "The Interaction of *Candida boidinii* Formate Dehydrogenase with a New Family of Chimeric Biomimetic Dye–Ligands," *Arch. Biochem. Biophys.* 316(1):169–178 (1995).
Labrou et al., "Biomimetic–dye affinity chromatography for the purification of mitochondrial L–malate dehydrogenase from bovine heart," *J. Biotechnol.*, 45:185–194 (1996).
Lee et al., "Rapid corepressor exchange from the trp–repressor/operator complex: an NMR study of [ul–13C/15N]–L–tryptophan," *J. Biomol. NMR* 5(4):367–375 (1995).
LeMaster, "Deuteration in protein proton magnetic resonance," *Methods Enzymol.* 177:23–43 (1989).

(List continued on next page.)

*Primary Examiner*—Nashaat T. Nashed
(74) *Attorney, Agent, or Firm*—McDermott, Will & Emery

(57) ABSTRACT

Methods for rapidly identifying drug candidates that can bind to an enzyme at both a common ligand site and a specificity ligand site, resulting in high affinity binding. The bi-ligand drug candidates are screened from a focused combinatorial library where the specific points of variation on a core structure are optimized. The optimal points of variation are identified by which atoms of a ligand bound to the common ligand site are identified to be proximal to the specificity ligand site. As a result the atoms proximal to the specificity ligand site can then be us ed as a point for variation to generate a focused combinatorial library of high affinity drug candidates that can bind to both the common ligand site and the specificity ligand site. Different candidates in the library can then have high affinity for many related enzymes sharing a similar common ligand site.

62 Claims, 12 Drawing Sheets

OTHER PUBLICATIONS

Moore, "NMR techniques for characterization of ligand binding: Utility for lead generation and optimization in drug discovery," *Biopolymers* 51(3):221–243 (1999).

Moore, "NMR screening in drug discovery," *Curr. Opin. Biotechnol.* 10(1):54–58 (1999).

Morken et al., "Exploring the leucine–proline binding pocket of the Src SH3 domain using structure–based, split–pool synthesis and affinity–based selection," *J. Am. Chem. Soc.* 120:30–36 (1998).

Muchmore et al., "Expression and nitrogen–15 labeling of proteins for proton and nitrogen–15 nuclear magnetic resonance," *Methods Enzymol.* 177:44–73 (1989).

Pervushin et al., "Attenuated $T_2$ relaxation by mutual cancellation of dipole–dipole coupling and chemical shift anisotropy indicates an avenue to NMR Structures of very large biological macromolecules in solution," *Proc. Natl. Aad. Sci. USA* 94:12366–12371 (1997).

Pervushin et al., "Transverse Relaxation–Optimized Spectroscopy (TROSY) for NMR Studies of Aromatic Spin Systems, in $^{13}$C–Labeled Proteins," *J. Am. Chem. Soc.* 120:6394–6400 (1998).

Reilly and Fairbrother, "A novel isotope labeling protocol for bacterially expressed proteins," *J. Biomolecular NMR* 4:459–462 (1994).

Reinstein et al., "Fluorescence and NMR investigations on the ligand binding properties of adenylate kinases," *Biochem.* 29:7440–7450 (1990).

Rozwarski et al., "Modification of the NADH of the isoniazid target (INhA) from *mycobacterium tuberculosis*," *Science* 279:98–102 (1998).

Salzmann et al., "TROSY–type Triple–Resonance Experiments for Sequential NMR Assignments of Large Proteins," *J. Am. Chem. Soc.*, 121:844–848 (1999).

Scheffzek et al., "Crystal structure of the complex of UMP/CMP kinase from *Dictyostelium discoideum* and the bisubstrate inhibitor $P^1$–(5'–Adenosyl) $P^5$–(5'–Uridyl) pentaphosphate (UP$_5$A) and Mg$^{2+}$ at 2.2 Å: implications for water–mediated specificity," *Biochem.* 35:9716–9727 (1996).

Sem and Kasper, "Geometric relationship between the nicotinamide and isoalloxazine rings in NADPH–cytochrome P–450 oxidoreductase: implications for the classification of evolutionarily and functionally related flavoproteins," *Biochem.* 31:3391–3398 (1992).

Sem et al., "NMR Spectroscopic Studies of the DNA–binding Domain of the Monomer–binding Nuclear Orphan Receptor, Human Estrogen Related Receptor–2," *J. Biological Chem.* 272(29):18038–18043 (1997).

Sem and Coutts, "Accelerating Drug Discovery at Triad Biotechnology," *Solutions,* pp. 9 (1998).

Sem and Coutts, "Accelerating Drug Discovery at Triad Biotechnology," *Solutions,* pp. 11 (1998).

Shuker et al., "Discovering High–Affinity Ligands for Proteins: SAR by NMR," *Science* 274:1531–1534 (1996).

van Nuland et al., "The NMR determination of the IIA$^{mtl}$ binding site on HPr of the *Escherichia coli* phosphoenol pyruvate–dependent phosphotransferase system," *FEBS,* 315:11–15 (1993).

Venters et al., "High–level $^2$H/$^{13}$C/$^{15}$N labeling of proteins for NMR studies," *J. Biol. NMR* 5:339–344 (1995).

Wemmer and Williams, "Use of nuclear magnetic resonance in probing ligand–macromolecule interactions," *Methods Enzymol.* 239:739–767 (1994).

Wüthrich, "The Second decade–into the thrid millenium," *Nature Structural Biology* Nature Structural Biology NMR Supplement: 492–495 (1998).

Yamazaki et al., "A suite of triple resonsance NMR experiments for the backbone assignment of $^{15}$N, $^{13}$C, $^2$H labeled proteins with high sensitivity," *J. Am. Chem. Soc.* 116:11655–11666 (1994).

Li et al., "The inter–ligand Overhauser effect: A powerful new NMR approach for mapping structural relationships of macromolecular ligands," *J. Biomol. NMR,* 15:71–76 (1999).

Medek et al., "The Use of Differential Chemical Shifts for Determining the Binding Site Location and Orientation of Protein–Bound Ligands," *J. Am. Chem. Soc.,* 122:1241–1242 (2000).

* cited by examiner

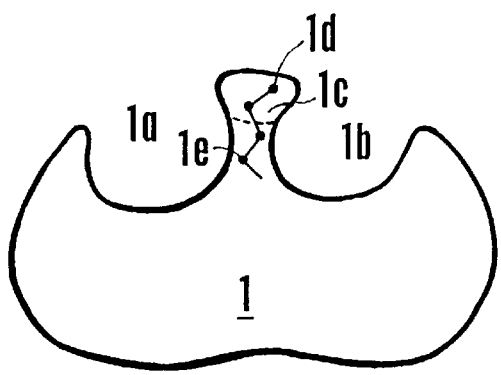
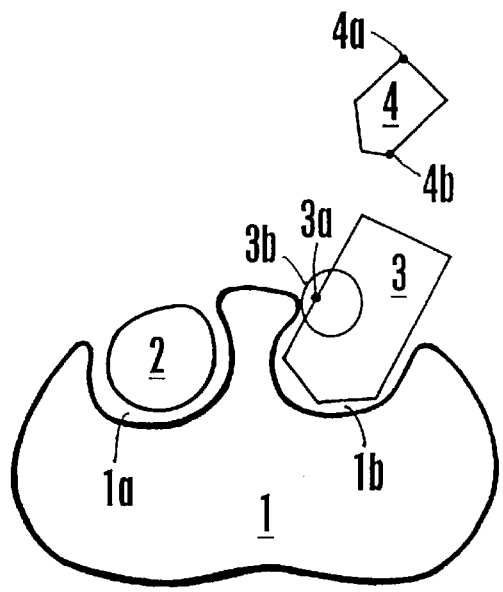
Fig. 1A    Fig. 1B
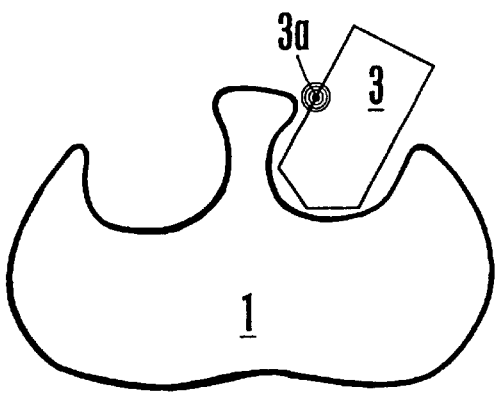
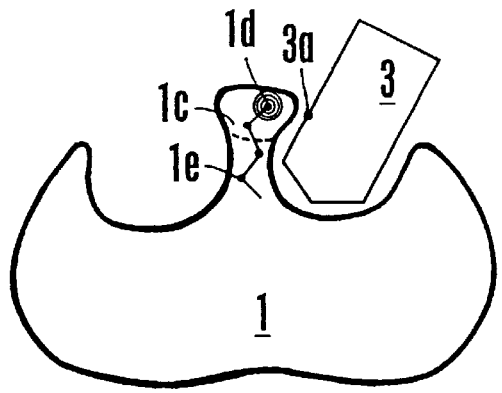
Fig. 2A    Fig. 2B

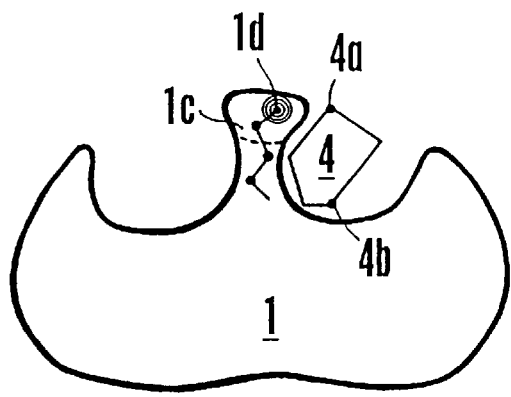
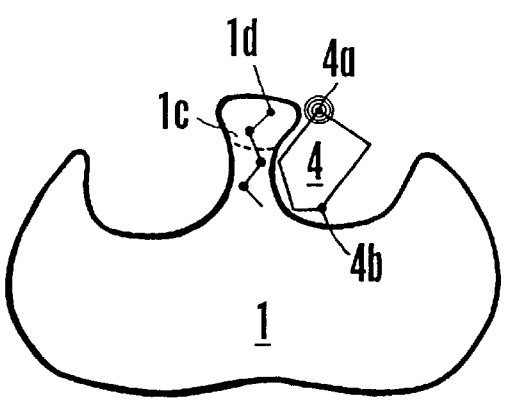
Fig. 3A  Fig. 3B
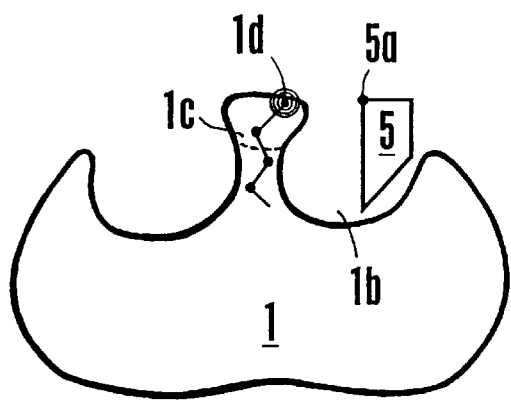
Fig. 3C

Fig. 4A
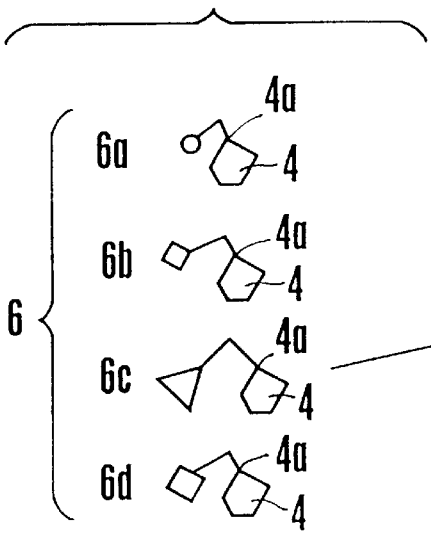
Fig. 4B
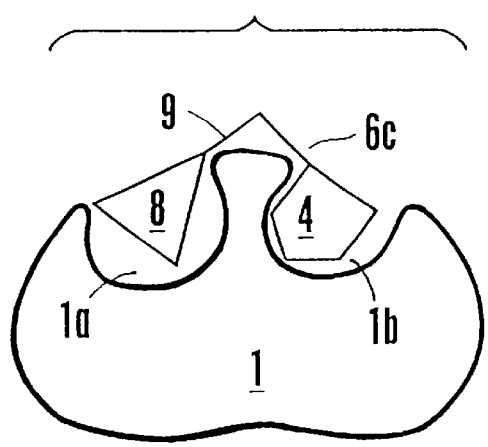
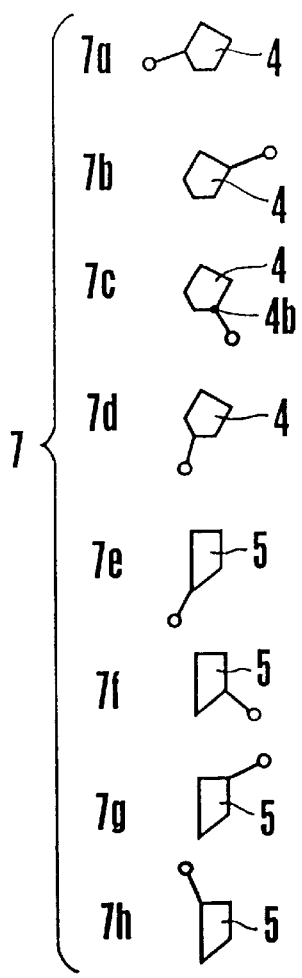

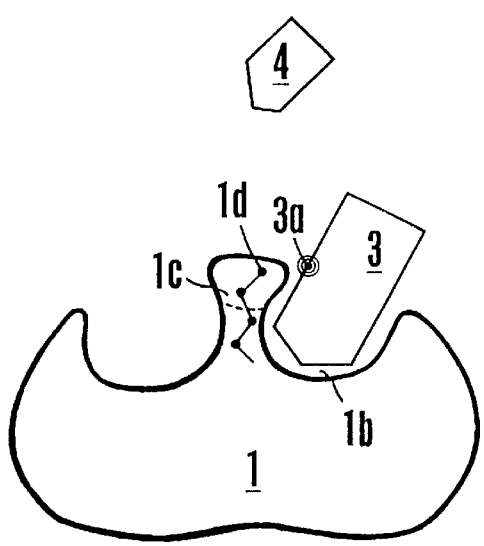
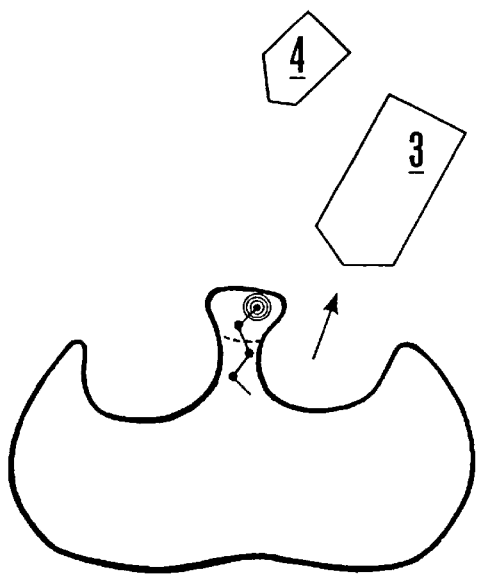
Fig. 5A
Fig. 5B
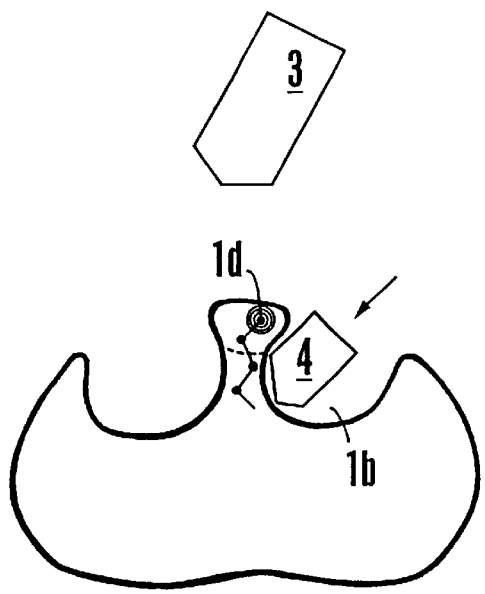
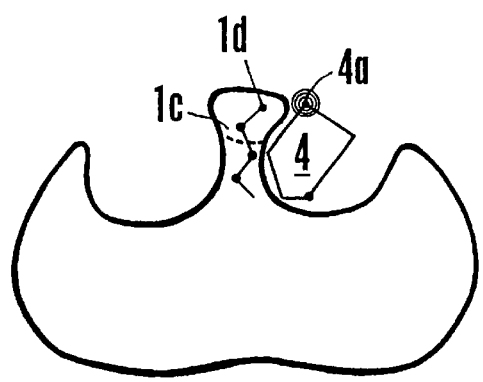
Fig. 5C
Fig. 5D

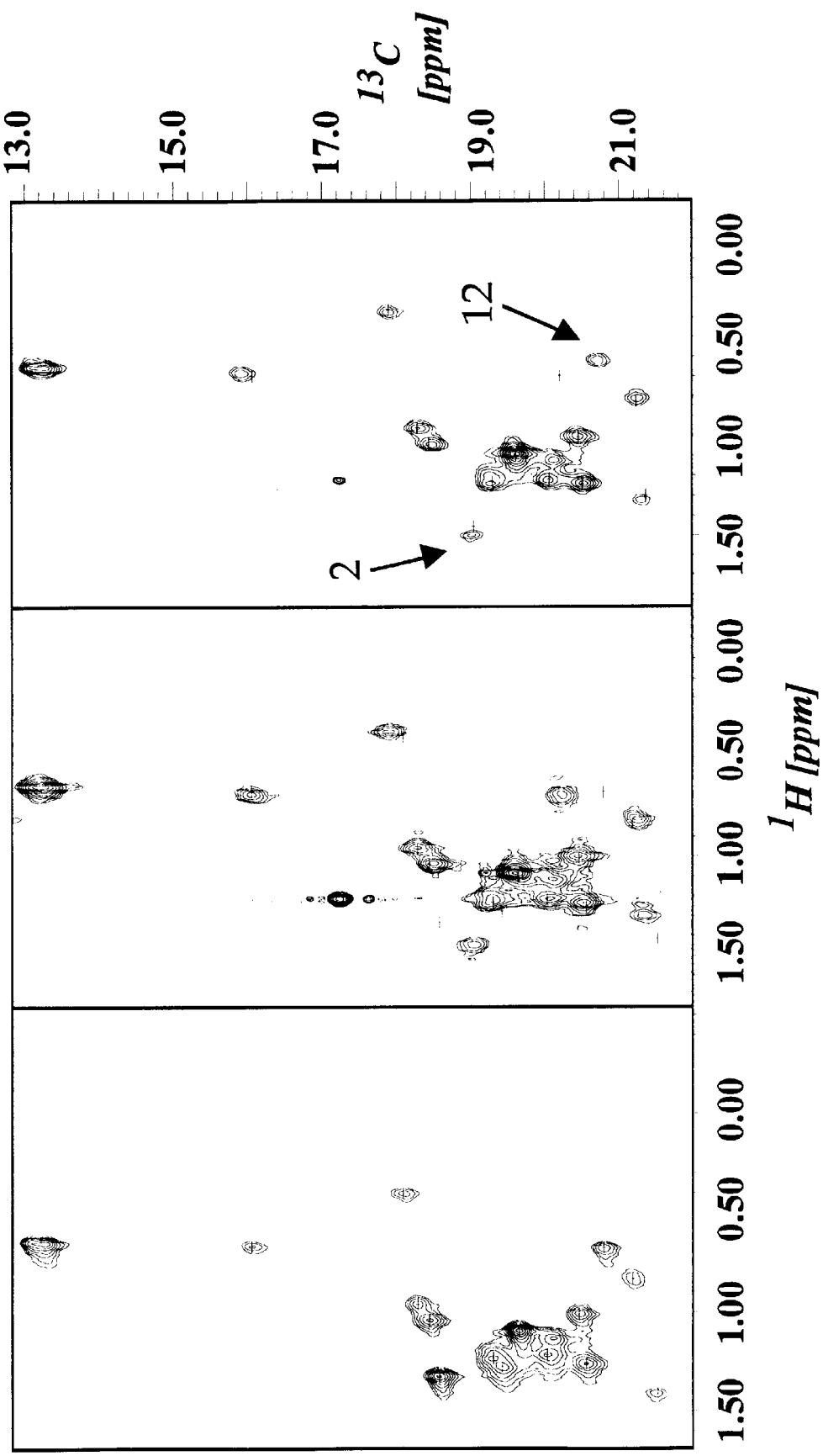

Figure 11

| Free DHPR Thr δ (ppm) | | DHPR + NADH Thr δ (ppm) | | DHPR + AcNADH Thr δ (ppm) | | Δδav* NADH | Δδav* AcNADH | dΔδ** | Peak # |
|---|---|---|---|---|---|---|---|---|---|
| $^1$H | $^{13}$C | $^1$H | $^{13}$C | $^1$H | $^{13}$C | | | | |
| 1.41 | 21.50 | 1.31 | 21.46 | 1.31 | 21.50 | 0.0591 | 0.0589 | 0.0002 | 1 |
| 1.33 | 18.57 | 1.45 | 19.04 | 1.50 | 19.01 | 0.0910 | 0.1136 | -0.0226 | 2 |
| 1.28 | 19.41 | 1.11 | 19.74 | 1.11 | 19.74 | 0.1090 | 0.1080 | 0.0010 | 3 |
| 1.26 | 20.54 | 1.24 | 20.50 | 1.23 | 20.51 | 0.0128 | 0.0181 | -0.0053 | 4 |
| 1.23 | 19.29 | 1.23 | 19.29 | 1.23 | 19.27 | 0.0000 | 0.0024 | -0.0024 | 5 |
| 1.21 | 20.01 | 1.22 | 20.05 | 1.22 | 20.02 | 0.0077 | 0.0060 | 0.0017 | 6 |
| 1.10 | 19.64 | 1.10 | 19.61 | 1.09 | 19.58 | 0.0037 | 0.0094 | -0.0057 | 7 |
| 1.04 | 18.43 | 1.04 | 18.43 | 1.04 | 18.43 | 0.0000 | 0.0000 | 0.0000 | 8 |
| 1.01 | 20.44 | 1.01 | 20.44 | 1.00 | 20.44 | 0.0000 | 0.0059 | -0.0059 | 9 |
| 0.96 | 18.28 | 0.96 | 18.28 | 0.96 | 18.28 | 0.0000 | 0.0000 | 0.0000 | 10 |
| 0.83 | 21.17 | 0.83 | 21.22 | 0.81 | 21.23 | 0.0061 | 0.0139 | -0.0078 | 11 |
| 0.68 | 20.78 | 0.70 | 20.19 | 0.62 | 20.70 | 0.0729 | 0.0367 | 0.0362 | 12 |
| 0.67 | 16.05 | 0.70 | 16.07 | 0.68 | 15.89 | 0.0178 | 0.0203 | -0.0025 | 13 |
| 0.40 | 18.08 | 0.36 | 17.89 | 0.37 | 17.89 | 0.0331 | 0.0291 | 0.0040 | 14 |

*$\Delta\delta_{av}$ = SQRT{[($\Delta\delta H^2/1.44$) + ($\Delta\delta C^2/33.7$)]/2}

**$d\Delta\delta_{av}$ = $\Delta\delta_{av}$(NADH) - $\Delta\delta_{av}$(AcNADH)

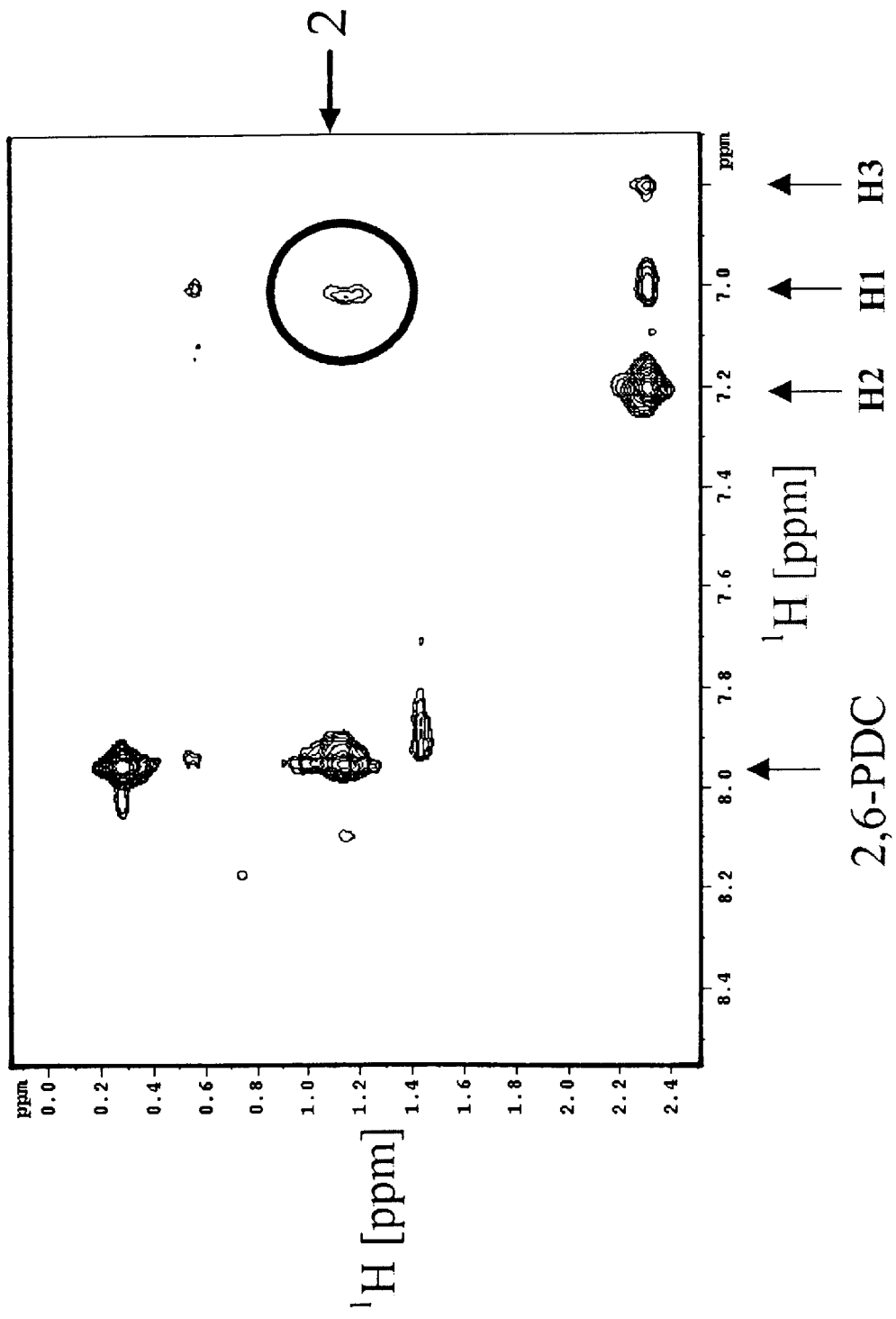

NMR-SOLVE METHOD FOR RAPID IDENTIFICATION OF BI-LIGAND DRUG CANDIDATES

This application is a continuation-in-part of application Ser. No. 09/326,435, filed Jun. 4, 1999, now U.S. Pat. No. 6,333,149 the content of which is hereby incorporated by reference.

BACKGROUND OF THE INVENTION

1. Field of the Invention

The present invention relates to drug discovery methods, more specifically to NMR methods for identifying atoms of interest in enzyme ligands for generating and screening combinatorial libraries of bi-ligand drug candidates.

2. Background Information

Widespread and sometimes indiscriminate use of antibiotics has allowed certain strains of disease-causing bacteria to become resistant to commonly available antibiotics. As a result, the need for more. effective antimicrobial drugs is becoming more pressing. One approach to developing such drugs is to find compounds that bind to essential enzymes in bacteria. When such enzymes have two adjacent binding sites, it is especially useful to find "bi-ligand" drugs that can bind at both sites simultaneously. Such drugs are likely to bind extremely tightly, inactivating the enzyme and ultimately killing the bacteria.

The rapid discovery and development of bi-ligand drugs has been difficult. Bi-ligand drug candidates have been identified using rational drug design, but previous methods are time-consuming and require a precise knowledge of structural features. When searching for a drug that binds to an enzyme at two binding sites, it would be particularly useful to understand how a ligand binds to the enzyme. Specifically, which atoms in the ligand interact with which portions of the enzyme's binding sites?

Recent advances in nuclear magnetic spectroscopy (NMR) have allowed the determination of the three dimensional interactions between a ligand and an enzyme in a few instances. However, these efforts have been limited by the size of the enzyme and can take years to map and analyze the complete structure of the complexes of enzyme and ligand.

Thus, there is a need to more rapidly identify, which atoms in the ligand interact with which portions of the enzyme binding sites so that focused combinatorial libraries can be generated and screened for more effective drugs. The present invention satisfies this need and provides related advantages as well.

SUMMARY OF THE INVENTION

The present invention provides a method for rapidly identifying drug candidates that can bind to an enzyme having at least two binding sites. The first site on the enzyme is the "common ligand site" where a known ligand can bind to the enzyme, as well as to other related enzymes. The second site is a "specificity ligand site" adjacent to the common ligand site. Thus, the method identifies bi-ligand drug candidates that can bind at both the common ligand site and the specificity ligand site. As a result, the candidates can bind with high affinity to the enzyme. As a further result, the candidates can be used to bind to related enzymes sharing a similar common ligand site.

The bi-ligand drug candidates are screened from a combinatorial library. Like other combinatorial libraries, a number of diverse compounds can be generated off of a core structure. In the case of a bi-ligand library, this core structure can be a mimic of the common ligand. The mimic can then be derivatized with varying groups at a selected point to generate the diversity of drug candidates in the library. The library is "focused" by optimizing the specific points on the mimic where variation occurs.

The optimal points of variation on the ligand are identified by determining which atoms are proximal to the specificity ligand site when the mimics bound to the common ligand site. These atoms are identified by first determining which amino acids of the enzyme are proximal to the specificity ligand site, and then identifying which atoms on the bound common ligand mimic are proximal to these amino acids. NMR methods using the nuclear Overhauser effect (NOE) are particularly useful for identifying proximal atoms. Accordingly, this technique has been named Nuclear Magnetic Resonance-Structure Oriented Library Valency Engineering or NMR-SOLVE$^{SM}$. As a result of NMR-SOLVE$^{SM}$, the identified proximal atoms can then be used as a point for Variation to generate a focused combinatorial library of high affinity drug candidates that can bind to both the common ligand site and the specificity ligand site of an enzyme of interest, as well as related enzymes sharing a similar common ligand site.

BRIEF DESCRIPTION OF THE DRAWINGS

FIG. 1a shows a schematic enzyme 1 having a specificity ligand site (SL site) 1a and a common ligand site (CL site) 1b. For purposes of illustration, an interface region 1c is shown between the SL site 1a and the CL site 1b. Enzyme atom 1d is within the interface region 1c and enzyme atom 1e is outside the interface region 1c. FIG. 1b shows a specificity ligand (SL) 2 bound to the SL site 1a and a common ligand (CL) 3 bound to the CL site 1b. The CL 3 has a reactive atom 3a within a reactive region 3b. A nonbound common ligand mimic (CL mimic) 4 is also shown, having individual atoms 4a, 4b.

FIG. 2 illustrates the first stage of identifying an atom 1d of the interface region 1c that is proximal to the reactive atom 3a of the CL 3. In FIG. 2a, the nucleus 6f the reactive atom 3a of the CL 3 is perturbed. In turn, the nucleus of a nearby atom 1d in the interface region 1c of the enzyme 1 becomes perturbed, as shown in FIG. 2b. The nucleus of atom 1e, which is outside of the interface region 1c, is more distant from the reactive atom 3a and is not detectably perturbed. Thus, detection of the perturbation of the nucleus of nearby atom 1d allows its identification as an atom proximal to the reactive atom 3a of the CL 3.

FIG. 3 illustrates the second stage of identifying which CL mimics are proximal to the interface region 1c and identifying an atom 4a of the CL mimic 4 that is proximal to the part of the interface region 1c identified as 1d. In FIG. 3a, the nucleus of atom 1d previously identified in the interface region 1c is perturbed. The nucleus of an atom 4a in the CL mimic 4 then becomes perturbed, as shown in FIG. 3b, but not a the nucleus of atom 4b, which is more distant from interface atom 1d. Consequently, an atom 4a of the CL mimic 4 is identified that is proximal to the part of the interface region 1c identified as 1d. As a further benefit, FIG. 3c illustrates that the second stage can determine whether a particular CL mimic binds to the CL site 1b, but does not bind proximally to the interface region 1c. Thus, if the nucleus of interface atom 1d perturbed, it will be too distant from atoms of the distally binding CL mimic 5 so that the nucleus of atom 5a does not become perturbed.

Once a proximal atom 4a has been identified in the CL mimic 4, FIG. 4a illustrates a focused combinatorial library 6 of bi-ligand drug candidates 6a, 6b, 6c and 6d, having varying substituent groups attached to the identified proximal atom 4a. These are in contrast to drug candidates 7a to 7h from an unfocused combinatorial library 7 based on substitutions at other atoms such as 4b of the CL mimic 4 or substitutions to a distally binding CL mimic 5. Upon screening the focused library 6, a particular drug candidate 6c is selected for high binding affinity to the enzyme. As shown in FIG. 4b, the drug candidate;6c consists of the CL mimic 4 attached to a SL-binding moiety 8 through a linker 9. The drug candidate 6c can then bind the enzyme 1 tightly at both the SL site 1a and the CL site 1b.

FIG. 5 illustrates a variant method for identifying a proximal atom 4a. In FIG. 5a, a CL 3 is bound to the CL site 1b in the presence of nonbound CL mimic 4. The nucleus of an atom 3a of the CL 3 is perturbed with radio frequency irradiation, transferring energy to a nearby atom 1d of the interface region 1c in an NOE experiment. The CL3 then unbinds, as in FIG. 5b. In FIG. 5c, a CL mimic 4 then binds to the CL site 1b, so that the energy is then transferred from the atom 1d of the interface region 1c to a nearby atom 4a of the CL mimic 4, as shown in FIG. 5d. As a result, the variant method allows identification of an atom 4a of the CL mimic 4 that is proximal to the interface region 1c.

FIG. 6 illustrates the identification of amino acids at the interface region.

FIGS. 8 to 13 illustrate the results discussed in Example II.

FIG. 9 shows the 2-D structures of the SL mimic 2,6-pyridinedicarboxylate (2,6-PDC) (FIG. 9a), the common ligand NADH (FIG. 9b), and CL analog AcNADH (FIG. 9c), which is used for perturbation by chemical modification. AcNADH differs from NADH by a substitution from amine in NADH to methyl in AcNADH, shown at the far right of FIGS. 9b and 9c. Furthermore, individual protons $H_{1'A}$, $H_{8A}$ and $H_{2N}$ on AcNADH and corresponding atoms on NADH are indicated.

FIG. 10 illustrates step (a) of the method of the invention, showing $^1H$—$^{13}C$ HMQC spectra of threonine-labeled apo DHPR in the absence of ligand (FIG. 10a), in the presence of common-ligand NADH (FIG. 10b) and in the presence of CL-analog AcNADH (FIG. 10c). Peaks 2 and 12 are indicated with arrows.

FIG. 11 provides a chemical shift list of threonine residues in DHPR. The list separately provides the $^1H$ and $^{13}C$ chemical shifts for free DHPR (from FIG. 10a), DHPR bound to common ligand NADH (from FIG. 10b) and DHPR bound to CL analog AcNADH (from. FIG. 10c). Cross-peaks were arbitrarily assigned numbers. The list then tabulates the changes in $^{13}C$ and $^1H$ shifts between free DHPR and DHPR bound to NADH ($\Delta\delta$a v NADH), and then tabulates the changes between free DHPR and DHPR bound to AcNADH ($\Delta\delta$av AcNADH). The shifts were quantitated according to the starred equations shown. Shifts were normalized for proton ($\div1.44$) and carbon ($\div33.7$) chemical shift dispersion in the methyl region. The differences between these comparisons are further compared ($\Delta\delta$av NADH versus $\Delta\delta$av AcNADH) to identify potential atoms in the interface region.

FIG. 12 also illustrates step (a) of the invention, showing the 2D-NOESY spectrum of the binary complex of DHPR with CL analog AcNADH. The mixing time was 200 msec. Atoms of AcNADH are as defined in FIG. 9c. Chemical shift A corresponds to a methyl group on a threonine in a part of the CL site remote from the interface region that is close to atoms $H_{8A}$ and $H_{1'A}$ in AcNADH. In contrast, chemical shift B is for the atom corresponding to cross-peak #2 in FIG. 10c, with a proton chemical shift of 1.5 ppm. This atom is close to proton $H_{2N}$ in AcNADH, thereby confirming $H_{2N}$ as an proton proximal to the interface region.

FIG. 13 illustrates step (b) of the method of the invention. The 2D NOESY spectrum is of the ternary complex of DHPR with the CL mimic TTE0001.002.D2 (FIG. 8a) and an SL analog, 2,6-PDC (see FIG. 9a). The SL analog was used to promote a closed conformation for the enzyme. The atoms of TTE0001.002.D2 are as defined in FIG. 8a. Cross-peak #2 corresponds to cross-peak #2 in FIG. 10c. There is a slightly different proton chemical shift because SL mimic 2,6-PDC is bound, as well as because the CL mimic rather than AcNADH is bound. As a result, H1 is identified as an atom on the CL mimic. TTE0001.002.D2 proximal the interface region, since H1 is known to have a proton chemical shift of 7.0 ppm from independent assignments using 2D COSY and 1D proton spectra.

DETAILED DESCRIPTION OF THE INVENTION

Figure 6A:
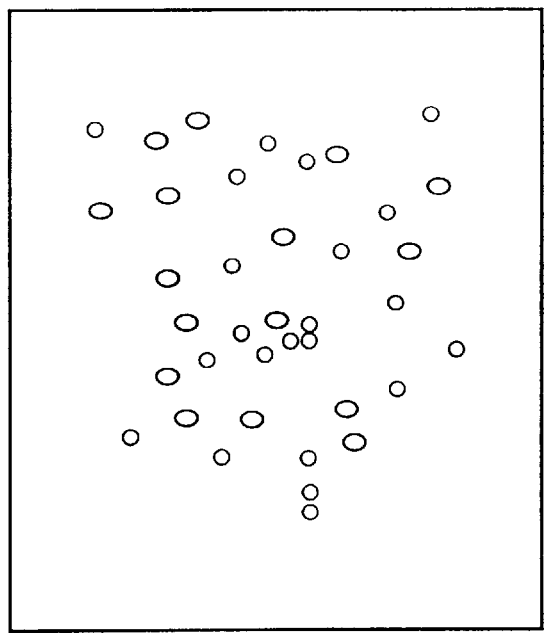
FIG. 6a shows the results of a 2D-HSQC NMR experiment with TROSY for an NADH-bound dehydrogenase.

The present invention provides methods for generating focused combinatorial libraries and for screening them for drug candidates that can bind tightly to certain enzymes. The libraries are "focused" by selecting the best core'structures and optimizing the location of variations applied to a given core structure, which serves as a platform for the particular library. Focusing the variations to a limited set of points on the core structure reduces the number of compounds to be generated and accelerates the drug discovery process. Using a core structure that binds to a common site shared by members of a gene family can also make the library generally useful for the other members. The variations in each library can be optimized by identifying specific atoms of interest in the core structure. For the purposes of the invention, the core structure is a ligand—or a chemical mimic to such a ligand—that binds to an enzyme.

The term "enzyme" herein means any protein that catalyzes a biochemical reaction. Proteins having non-aminoacid modifications such as glycosylation or containing other non-proteinaceous components such as metal ion prosthetic groups are included within this definition.

Enzymes useful in the invention are not limited by their size. For example, an enzyme can have a monomer molecular weight greater than 15, 25, 30, 35 or 45 kD. An enzyme can also have a complete molecular weight greater than 30, 50, 75, 100 or 150 kD. An enzyme can also have a monomer molecular weight less than 120, 100, 80, 60 or 40 kD, or a complete molecular weight less than 200, 150, 100 or 50 kD. The term "molecular weight" herein means the sum of the atomic weights of all the atoms in the molecule. The molecular weight can be estimated using well known techniques such as SDS-PAGE under reducing or non-reducing conditions. Molecular weights can also be determined using mass spectrometry, such as FAB, which includes cesium ion bombardment, electrospray ionization (ESI) and matrix-assisted laser desorption ionization (MALDI).

The enzyme can be obtained from any natural source such as human subjects, primates, mammals, animals, plants, fungi or bacteria, including any derived cell or tissue cultures. In particular, the enzyme can be from a human or animal pathogen. An enzyme can also be derived originally from a natural source, but later modified by artificial means, for example a recombinant enzyme or chemically modified enzyme.

The enzyme can also be a member of a gene family. The term "gene family" herein means a group of genes—or proteins encoded by such genes—often derived by duplication and variation from a common ancestral gene, exhibiting sequence homology and related phenotypic functions. More specifically, a gene family is a family of proteins that can all bind a common ligand such as NADH or ATP. As such, gene family members can often be identified by the presence of a conserved amino acid sequence motif. Several large gene families have been identified, including families as large as 20, 50, 100 and even 200 members. Two particular examples of a gene family are kinases and oxidoreductases. The term "kinase" herein means any enzyme that catalyzes the transfer of a phosphoryl group from ATP or other nucleoside triphosphate to another compound. The term "oxidoreductase" herein means any enzyme that catalyzes an oxidation-reduction reaction. Still other gene families include transaminases, decarboxylases and methyltransferases, as well as families of farnesyl-, geranyl-, geranyl-geranyl- and ubiquitin-transferring enzymes.

Another particular gene family is the dehydrogenase gene family. The term "dehydrogenase" herein means any enzyme that catalyzes the removal of hydrogen from a substrate using a compound other than molecular oxygen as an acceptor. Typically the hydrogen is transferred to the coenzyme $AND^+$ (nicotinamide adenine dinucleotide) or $NADP^+$ (nicotinamide adenine dinucleotide phosphate). The dehydrogenase gene family is large, comprising approximately 17% of all enzymes (You, Kwan-sa, "Stereospecificity for Nicotinamide Nucleotides in Enzymatic and Chemical Hydride Transfer Reactions," *CRC Crit. Rev. Biochem.* 17:313–451 (1985)). A particularly useful enzyme is dihydrodipicolinate reductase (DHPR), which is 28 kD in monomer form, and is a tetramer in solution. Thus, the dehydrogenase family is likely to be a rich source of drug targets.

The three-dimensional structures of several dehydrogenases are known, including dogfish lactate dehydrogenase, soluble porcine malate dehydrogenase, horse liver alcohol dehydrogenase, lobster glyceraldehyde-3-phosphate dehydrogenase and *Bacillus stearothermophilus* glyceraldehyde-3-phosphate dehydrogenase (apo form). Based on these structures, it is now understood that dehydrogenases share several conserved features, including two characteristic domains.

The first domain conserved among the dehydrogenases contains a site that can bind $AND^+$, $NADP^+$ or a similar hydrogen acceptor (Bellamacina, C. R., "The Nicotinamide Dinucleotide Binding Motif: A Comparison of Nucleotide Binding Proteins," *FASEB J.* 10:1257–1269 (1996)). Because the $AND^+$ ligand that can bind at such a site is shared in common with other members of the gene family, the $AND^+$-binding site can be described as a common ligand site. The term "common ligand site" herein means a location on any enzyme where a common ligand can bind.

The term "common ligand" or "CL" herein means a molecule that can selectively bind at a site on an enzyme. A particularly useful CL can bind to a site conserved in a family of enzymes. The term can therefore extend to molecules that can bind to members of a gene family.

A useful CL is a cofactor. The term "cofactor" herein means any small molecule that binds in the CL site and serves as a co-substrate when bound to an enzyme. Cofactors often contain a nucleotide such as adenine mononucleotide or nicotinamide mononucleotide. Examples of such cofactors include ATP, ADP and SAM (S-adenosyl methionine). Another group of cofactors that contain a nucleotide is the group $AND^+$, NADH, $NADP^+$ and NADPH. Other such cofactors include $FMNH_2$, FMN, FAD, $FADH_2$, CoA, GTP and GDP. Still other cofactors include THF, DHF, TPP, bidtin, dihydropterin, heme, farnesyl and farnesyl-pyrophosphate, geranyl, geranyl-geranyl, ubiquitin, pyridoxal phosphate and thiamine pyrophosphate.

CLs can have at least one atom involved in the reaction catalyzed by the enzyme. In the case of NADH, this "reactive atom" is a hydrogen atom attached to the carbon-4 position of the nicotinamide ring, which is transferred as a hydride ion. For purposes of definition, a "reactive region" of the common ligand can be defined to encompass the reactive atom as well common ligand atoms that are immediately adjacent to the reactive atom. The reactive region also encompasses atoms of the common ligand that are immediately adjacent to the specificity ligand. In this definition, "immediately adjacent" means within 5 Ångstroms, but can be within 2, 3, 4 or 6, 7 or 8 Ångstroms. In functional terms, it can also mean sufficiently close that a chemical perturbation of the nucleus in one atom can be detected in a second atom, using NMR methods disclosed in greater detail below. Thus, a reactive region can mean the reactive atom itself as well as atoms of the common ligand that are immediately adjacent to the reactive atom or common ligand atoms immediately adjacent the SL. Since the reactive atom of a CL can react with an SL chemically, it is located at the interface of the CL and SL binding sites at some point in time.

Although the common ligands can be naturally occurring cofactors or molecules, the term also extends to chemical analogs that serve as mimics of the common ligand. Thus, "common ligand" should be understood to encompass "common ligand mimics."

The term "ligand mimic" herein means a molecule that can bind to the enzyme at the same site as the ligand. Thus, a CL mimic can displace a CL bound to an enzyme at the CL site. This property can be demonstrated by enzyme-binding competition assays between a natural common ligand and a common ligand mimic. The term can encompass molecules having portions similar to corresponding portions of the ligand in terms of structure or function. Because CLs can include CL mimics that are analogs of naturally occurring CLs, and because the scope of the term "CL mimic" can also encompass the original CL itself, the scdpe of the terms "CL" and "CL mimic" should be considered coextensive.

Examples of mimics to the common ligand NADH, for example cibacron blue, are described in *Dye-Ligand Chromatography*, Amicon Corp., Lexington Mass. (1980). In the case of cibacron blue, the similarity with NADH may not be immediately obvious from schematic drawings of their chemical structures, and may only become apparent when their three-dimensional structures are compared. Thus, even when it is known that cibacron blue can bind at NADH-binding sites on an enzyme, it may be difficult to assign correspondences between particular atoms in the CL and the CL mimic.

Numerous other examples of NADH-mimics, including useful modifications to obtain such mimics, are described in Everse et al. (eds.), *The Pyridine Nucleotide Coenzymes*, Academic Press, New York N.Y. (1982). Particular analogs include nicotinamide 2-aminopurine dinucleotide, nicotinamide 8-azidoadenine dinucleotide, nicotinamide 1-deazapurine dinucleotide, 3-aminopyridine adenine dinucleotide, 3-diazoacetylpyridine adenine dinucleotide and 5-aminonicotinamide adenine dinucleotide. Particular CL mimics can be identified and selected by liganddisplacement assays, as is well known in the art. CL mimic candidates can also be identified by searching databases of compounds for structural similarity with the common ligand or a CL mimic.

Figure 8A:
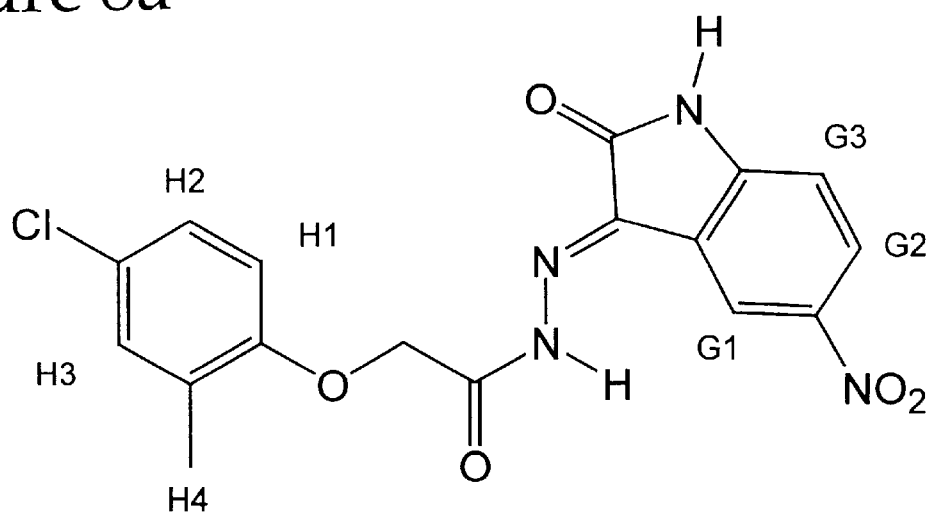
FIG. 8a shows the 2-D structure of the CL mimic designated TTE0001.002.D2. The Positions of protons H1, H2, H3, H4, G1, G2 and G3 on the CL mimic are indicated.
Figure 9A:
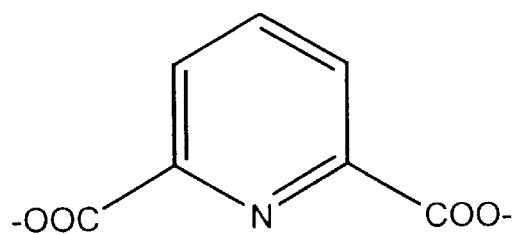
Figure 9B:
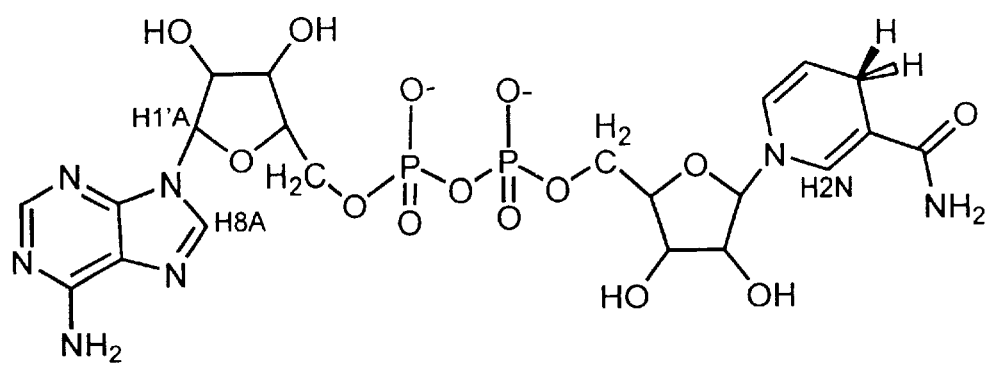

An example of a naturally occurring CL is NADH (FIG. 9b). Another CL is AcNADH (FIG. 9c), which is an analog of NADH. An example of a CL mimic is shown in FIG. 8a. When a CL or CL mimic has a structural or functional similarity to a known naturally occurring CL, such as between NADH and AcNADH, a reactive atom of a CL can be identified by analogy to the reactive atom of a known naturally occurring CL.

Unlike the first domain conserved among the dehydrogenases, the second domain can differ markedly among the individual enzymes and can bind a unique substrate from which the hydrogen is removed.

The term "specificity ligand" or "SL" herein means a molecule that can bind to a second site on the enzyme. A particularly useful SL can bind to a unique or a relatively small subset of a gene family, where the family shares binding properties with a single CL. Accordingly, the term "specificity ligand site" is the location where the specificity ligand can bind to an enzyme.

While specificity ligands can be naturally occurring molecules, they can also be chemical analogs that serve as mimics to naturally occurring molecules. These can be referred to as SL mimics, although "specificity ligand" should be understood to encompass "specificity ligand mimics" as well. Because SLs can include SL mimics that are analogs of naturally occurring SLs, and because the scope of the term "SL mimic" can also encompass the original SL itself, the scope of the terms "SL" and "SL mimic" should be considered coextensive. Specificity ligands can also have a reactive atom and reactive region, corresponding to the reactive atom and reactive region defined for CLs above.

In summary, such enzymes can transfer a reactive atom between a SL bound at the SL site and a CL bound at the CL site. For example, an AND$^+$-dependent dehydrogenase can transfer a hydride ion from the SL to the CL, which is AND$^+$.

Given the catalytic function of dehydrogenases and other enzymes, it follows that the CL site and the SL site should be physically located in proximity in the enzyme's three-dimensional structure to facilitate transfer of the hydrogen or other reactive atom. In fact, the three-dimensional geometric relationship between the CL site and SL sites has been shown to be conserved in evolutionarily related dehydrogenases (Sem and Kasper, "Geometric Relationship Between the Nicotinamide and Isoalloxazine Rings in NADPH-Cytochrome P450 Oxidoreductase," *Biochemistry* 31:3391–3398 (1992)). Thus, the CL site and SL site are said to be "adjacent." The domains of a protein may move relative to each other, depending on a variety of factors, such as substrate binding, so the protein can be described as being in an open or closed conformation. Nevertheless, in practical terms, an atom of the CL site and an atom of the SL site are at some point in time at most 3, 4, 5, 6, or 7 Å apart.

The portion of the enzyme between the adjacent CL and SL sites can be defined as the "interface region." In FIG. 1a, the interface region is shown schematically as 1c. Because an SL bound at the SL site can have similar properties as enzyme atoms of the interface region, the term "interface region" can also encompass atoms of an SL if an SL is bound to the enzyme at the SL site.

While the enzymes have been discussed in reference to dehydrogenases for purposes of illustration, it should be understood that any other enzyme will be useful in the invention so long as (1) the enzyme can bind a CL or a CL mimic at a CL site and binds an SL at an adjacent SL site; (2) an interface region can be defined as the atoms of the enzyme between the CL site and SL site, including atoms of a SL if bound to the enzyme; (3) the enzyme catalyzes a reaction involving a SL and a reactive atom of a CL; and (4) a CL reactive region can be defined as the reactive atom of the CL and CL atoms immediately adjacent to the reactive atoms or CL atoms immediately adjacent to the SL.

To prepare an enzyme for use in the method of the invention, the enzyme can be isolated or expressed by recombinant methods, harvested and purified by any conventional method well known in the art. A: particularly useful enzyme can be isotopically labeled with $^2$H, $^{13}$C, $^{15}$N or any combination of these isotopes (Venters et al., "High-level $^2$H/$^{13}$C/$^{15}$N Labeling of Proteins for NMR Studies," *J. Biomol. NMR* 5:339–344 (1995)). Following such labeling, deuterated amides can be exchanged with protons, depending on the particular NMR method used, as discussed below. A high level of amino-acid-specific protonation can be re-introduced in the protein. For example, to introduce protonation, this can be achieved by using directly protonated amino acids, or amino-acid precursors when the protein is expressed in bacteria (Rosen et al., "Selective Methyl Group Protonatioh of Perdeuterated Proteins," *J. Mol. Biol.* 263:627–636 (1996)). The amino acids that are particularly -useful contain methyl groups, although any amino acids can be introduced.

Having disclosed enzymes and ligands useful in the invention, the present invention provides a method for identifying an atom of a common ligand mimic that is proximal to an interface region. The method comprises two separate stages. In the first stage, an atom of the interface region is identified that is proximal to the reactive region of the common ligand. Second, the atom identified in the first stage is used to identify an atom in the CL mimic that is proximal to the interface region. Because this atom will also be proximal to the SL site, the atom or immediately adjacent atoms can then serve as an optimal point of variation when generating a combinatorial library of bi-ligand compounds that can bind at both the CL and the SL sites.

The first stage is performed by binding a CL to the CL site of the enzyme. The SL may also be bound to the enzyme. Then, the nucleus of an atom of the CL reactive region is perturbed by any of the various methods disclosed in further detail below. Thus, the nucleus of an interface atom can be identified that is perturbed by the perturbation of the CL reactive region, and hence is proximal to the CL.

In the second stage, a CL mimic is bound to the CL site. Again, the SL may be bound to the enzyme. The nucleus of the interface atom identified during the first stage is then perturbed. As in the first stage, this perturbation then causes further perturbation in the nuclei of nearby atoms in the CL mimic, which can also be detected, thereby identifying an atom of the CL mimic that is proximal to the interface region.

As a comparison, nuclei of atoms of the CL mimic that are not proximal to the interface atom do not become perturbed during the second stage. Similarly, if a CL mimic is bound to the CL site so that its atoms are not proximal to the interface region, the nuclei of CL mimic atoms will also not become perturbed. Thus, only proximal atoms of the CL mimic are identified.

In addition to the general method for identifying proximal atoms disclosed above, several variations are also encompassed within the invention. These variant methods also provide the identity of atoms in the common ligand or CL mimic that are proximal to the interface region of the enzyme, and therefore also proximal to the SL site.

Where an atom of the interface region has already been identified in the enzyme, the method can proceed directly to the second stage. Such identification can be by any means available, such as by homology modeling, mutagenesis or limited assignment. Thus, the method can comprise the steps of (1) binding a CL mimic to the CL site; (2) perturbing the nucleus of the identified atom of the interface region; and (3) identifying an NMR cross-peak corresponding to the nucleus of an atom of the CL mimic that is perturbed by the perturbation of the interface atom, thereby identifying an atom of the CL mimic that is proximal to the interface region.

Another variation makes use of transient binding of CL and CL mimics at the CL site of the enzyme in a transferred NOE experiment. As shown in FIG. 5a, a CL is bound to the CL site in the presence of unbound CL mimic. The nucleus of an atom of the CL can be perturbed by radiofrequency irradiation in an NOE experiment so that energy is transferred from the reactive region CL atom to the interface region. The CL is then allowed to unbind, as shown in FIG. 5b. When a CL mimic binds at the same CL site, as shown in FIG. 5c, magnetization is transferred back from the interface region to perturb the nucleus of an atom in the CL mimic, as shown in FIG. 5d. As a result, an NMR cross-peak can be identified corresponding to the atom of the CL mimic proximal to the interface region.

Yet another variation involves the observation of NOEs on dissociated ligands. The nucleus of an interface atom of the enzyme is perturbed, for example by irradiation, followed by magnetization transfer to CL mimic bound to the enzyme. Upon; dissociation of the CL mimic from the enzyme, the NOE can then be observed before magnetization decay in the nonbound CL mimic. Thus, an atom of the dissociated CL mimic can be identified that was proximal to the interface region when bound to the CL site.

The term "perturb" herein means to affect the chemical shift, intensity or line shape of the NMR signal for a nucleu's so that the effect can be detected in an NMR experiment. Perturbation also includes causing a detectable change in nuclear spin relaxation rates (1/T2 and 1/T1).

A particular perturbation method is to chemically alter an atom or an immediately adjacent atom. An example is the chemical substitution of reactive region atoms, such as replacing hydrogen with deuterium. Another substitution is replacing an amide with a carboxylic acid. These substitutions alter the electronic and structural environment of nearby atoms in the interface region, which produces changes in their NMR chemical shifts. Other chemical alterations include the introduction of paramagnetic or quadrupolar nuclei.

For example, a reactive hydrogen in NADH or NADPH can be perturbed by replacing the hydrogen with deuterium, resulting in NADD or NADPD (Sem and Kasper, "Geometric Relationship between the Nicotinamide and Isoalloxazine Rings in NADPH-Cytochrome P-450 Oxidoreductase: Implications for the Classification of Evolutionarily and Functionally Related Flavoproteins," *Biochemistry* 31: 3391–3398 (1992)). In this sense, the perturbation from NADH to NADD can be considered to be either the chemical alteration itself or the particular differences in the NMR spectra of an enzyme binding NADH and the NMR spectra of an enzyme binding NADD. Similarly, the nucleus of an atom of the enzyme can be perturbed by site-directed mutagenesis so that the differences between the spectra of the original enzyme and the mutated enzyme can be detected.

Yet another method of perturbation is to irradiate the nucleus of an atom with radio frequency energy (Rf irradiation). The term "radio frequency energy" herein means oscillating electrical voltages, currents or electromagnetic fields with frequencies in the range of 10 to 1000 MHZ or $10^7$ to $10^9$ sec$^{-1}$. The frequency selected depends on the magnetic field strength and the corresponding. Larmor frequency for the nucleus of interest at that field strength. Thus, differences in NMR spectra can be observed in samples with and without irradiation.

In modern multidimensional NMR NOE experiments, excitation is performed at a range of frequencies simultaneously so that frequencies are read off axes in each dimension. The central frequency and frequency range is selected for a given nucleus type so that it will excite all of those nuclei in the molecule. For example, at an 11.7 Tesla magnetic field strength, protons are excited at 500.0 MHZ (the Larmor frequency), with a range of at least ±5000 Hz.

As a result of perturbing the nucleus of a particular atom, the nuclei of other nearby atoms can be perturbed as well. The nuclear Overhauser effect (NOE) can cause detectible changes in the NMR signal of a nucleus that is proximal to the perturbed nucleus. Here, NOE is meant to include steady state and transient NOE. The signal changes are the result of magnetization transfer to the proximal atoms. Since an NOE occurs by spatial proximity, not merely connection via chemical bonds, it is especially useful for determining distances between molecules. The term "proximal" herein means within a defined distance of one or more atoms of interest, where the defined distance is a function of the method used to perturb. Functionally, "proximal" can be defined as being within a distance where perturbation can be detected. When an NOE is used, the distance is usually 5 Ångstroms, but can be 2, 3, 4 or 6, 7 or 8 Ångstroms.

Perturbation—whether by chemical alteration of an atom or as a result of irradiation in an NOE experiment—can be detected and identified by a variety of known methods. Detectable changes in NMR signals include changes in intensity (NOE), location (chemical shift) or width. (linewidth). General NMR techniques for proteins, including multidimensional NMR experiments and determination of protein-ligand interactions can be found in David G. Reid (ed.), *Protein NMR Techniques*, Humana Press, Totowa N.J. (1997).

In practice, the perturbed nuclei of atoms in large molecules can be identified using a multidimensional multinuclear NMR method to identify NMR cross-peaks corresponding to the perturbed atoms. Heteronuclear NMR experiments are particularly useful with larger proteins as described in Cavanaugh et al., *Protein NMR Spectroscopy: Principles and Practice*, ch. 7, Academic Press, San Diego Calif. (1996). For example, two-dimensional NMR experiments can measure the chemical shifts of two types of nuclei. A well established 2-D method is the $^1$H—$^{15}$N heteronuclear single quantum coherence (HSQC) experiment. Another method is the heteronuclear multiple quantum coherence (HMQC) experiment. Numerous other variant experiments and modifications are known in the art including nuclear Overhauser enhancement spectroscopy experiments (NOESY), for example NOE experiments involving a $\{^1H,^1H\}$ NOESY step.

Ambiguity based on chemical shift overlap can be resolved by (a) introducing a third dimension for $^{15}$N or $^{13}$C chemical shift; (b) not decoupling to a heteroatom in one of the two dimensions, thus producing diagnostic $^1$H—$^{13}$C or $^1$H—$^{15}$N one bond coupling constants; or (c) using 2-D $^{13}$C—$^1$H or $^{15}$N—$^1$H HMQC or HSQC-$\{^1H,^1H\}$ NOESY variants.

Higher-dimensional NMR experiments can be used to measure the chemical shifts of additional types of nuclei and to eliminate problems with cross peak overlap if spectra are too-crowded. In particular, the NMR method used can correlate $^1$H, $^{13}$C and $^{15}$N (Kay et al., *J. Magn. Reson*. 89:496–514 (1990); Grzesiek and Bax, *J. Magn. Resoh*. 96:432–440(1992)), for example in an HNCA experiment. Other heteronuclear NMR experiments can be used so long as the transfer of magnetization to all CL and protein protons is only to or from amide protons on the protein, since all carbon-attached protons in the protein are replaced with deuterons. Such experiments include HNCO, HN(CO)CA, HN(CA)CO and HNCACB experiments.

Other experiments involve cross-peaks of NH, protons of protein at Asn, Gln, Arg and/or His. Similarly, the cross-peaks of the methyl protons of protein specifically $^{13}$C—$^1$H$_3$ labeled at Leu, Thr, Ile, Val, Ala and/or Met can be observed in NOESY, chemical shift perturbationor other experiments.

Particular multidimensional techniques for identifying compounds that can bind to target molecules are described in U.S. Pat. No. 5,698,401 to Fesik et al., and U.S. Pat. No. 5,804,390 to Fesik et al. Related publications include PCT publications WO 97/18469, WO 97/18471 and WO 98/48264. However, these techniques, sometimes described as "SAR by NMR," require the complete assignments and determination of the three-dimensional structure of the enzyme (Shuker et al., "Discovering High-Affinity Ligands for Proteins: SAR by NMR," *Science* 274:1531–1534 (1996); Hajduk et al., "Discovery of Potent Nonpeptide Inhibitors of Stromelysin using SAR by NMR," *J. Am. Chem. Soc*. 119:5818–5827 (1997)). As a result, identification of suitable ligands using SAR by NMR can be an undertaking of more than a year. Only by determining the multiple structures of the enzyme while complexed with different pairs of ligands can these techniques suggest ligands to be covalently joined and tested for binding affinity. In contrast, the method of the invention does not require determining the complete assignments or structure of the enzyme; instead, it rapidly provides sufficient information to generate a focused combinatorial library of bi-ligand inhibitors without providing excess information.

Recent advances in NMR spectroscopy have used transverse relaxation-optimized spectroscopy (TROSY) to achieve narrow line widths, substantially increasing resolution and sensitivity of multidimensional NMR experiments. As a result, NMR can be applied to larger molecules than previously possible, such as proteins up to 100 kD or larger (Pervushin et al., *J. Am. Chem. Soc*. 120:6394–6400 (1998); Salzman et al., "TROSY-type Triple-Resonance Experiments for Sequential NMR Assignments of Large proteins, *J. Am. Chem. Soc*. 121:844–848 (1999)). Deuterium labeling and decoupling has also been used to achieve narrow line widths, further enabling NMR methods to be applied to large proteins (Yamazaki et al., "a Suite of Triple Resonance NMR Experiments for the Backbone Assignments of $^{15}$N, $^{13}$C, $^2$H Labeled Proteins with High Sensitivity," *J. Am. Chem. Soc*. 116:11655–11666 (1994)).

Deuterium labeling is especially useful if all protons—except those on specific methyls, such as threonines—are replaced with deuterons. Such methyl protons should be readily detectable, even on large. proteins.

Figure 6B:
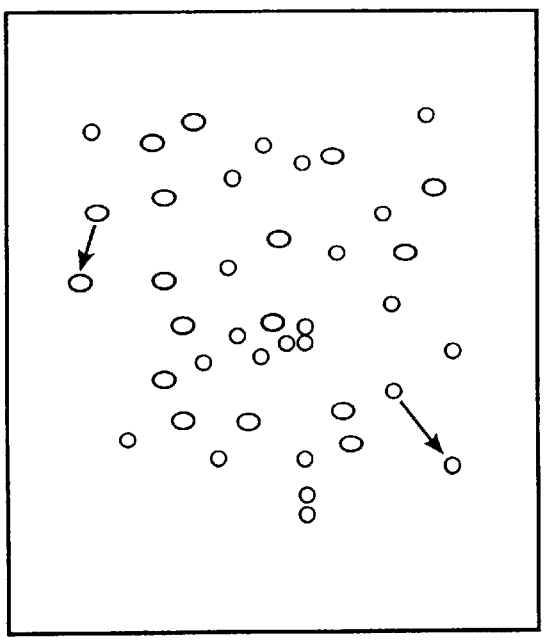
FIG. 6b shows thee results of a comparable experiment with an NADD-bound dehydrogenase, where the NADD has a deuterium-for-hydrogen-substitution on the 4-carbon position of the nicotinamide ring. As is wellknown, the 4-carbon of NADH is close to the interface region of dehydrogenases. In both figures, the x-axis represents the $^1H$ chemical shift and the y-axis represents the $^{15}N$ chemical shift. As a result of chemically perturbing the nucleus from NADH to NADD, changes in the chemical shifts—represented by the two arrows—permit identification of amino acids at the interface region of the enzyme.

Using the NMR methods disclosed above, atoms proximal to perturbed nuclei can be identified in the first stage by comparing NMR spectra with and without perturbation. As exemplified in FIG. 6, for example, NMR spectra from a 2D-HSQC experiment with TROSY can be compared for NADH-bound dehydrogenase and NADD-bound dehydrogenase. By comparing the spectra, NMR cross peaks can be identified that correspond to atoms most affected by the change in electronic and chemical environment resulting from substituting deuterium for hydrogen. As a result, the atoms in the NADH-binding site closest to the SL binding site, which are in the interface region, can be identified.

In order to know which cross peaks in the uncomplexed dehydrogenase correspond to the perturbed cross peaks in the NADD-dehydrogenase complex, it may be necessary to titrate the uncomplexed dehydrogenase with increasing concentrations of either NADH or NADD and monitor progressive changes in chemical shifts. Such a titration is not necessary if the corresponding cross peaks in the uncomplexed dehydrogenase can be identified by other means, such as the presence of a unique pair of $^{13}$C chemical shifts in the HNCA experiment.

Figure 7A:
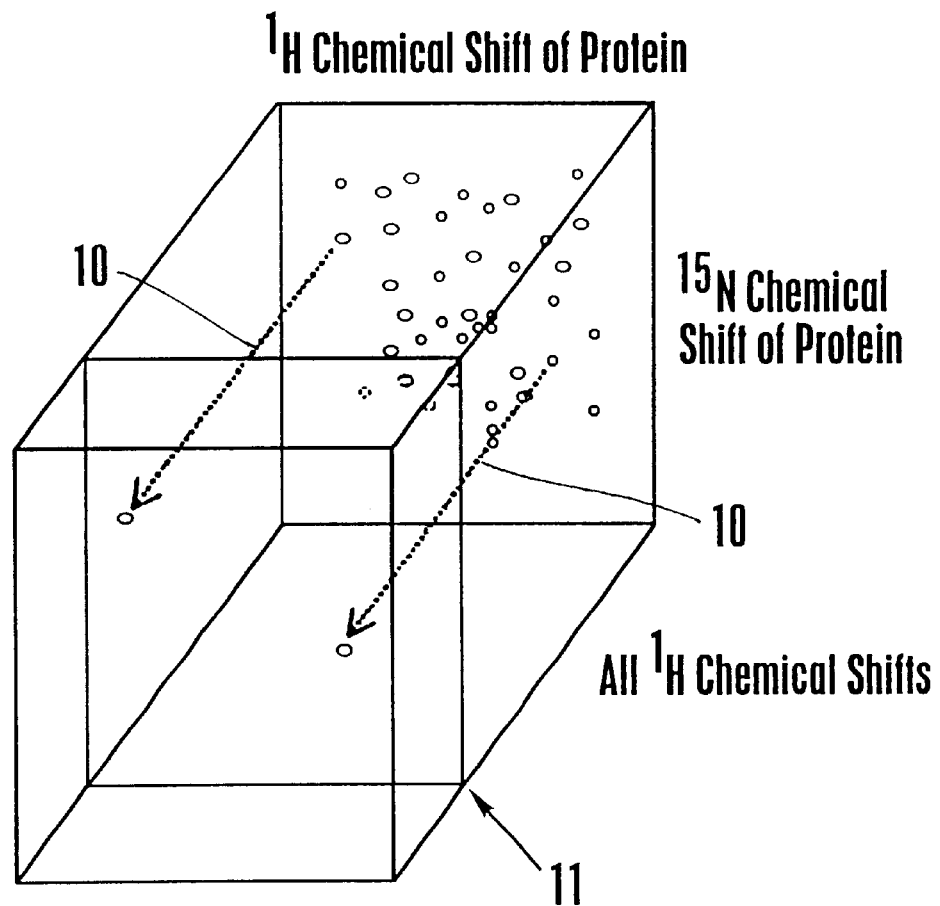
In FIG. 7a, the horizontal axis represents the $^1H$ chemical shift of protein, the vertical axis represents the $^{15}N$ chemical shift of protein and the oblique axis represents all $^1H$ chemical shifts. The broken arrows in FIG. 7a represent NOEs 10 resulting from radio frequency irradiation of the sample. These NOEs 10 are to ligand proton with chemical shift 11. The NOEs 10 allow identification of a proximal atom 4a of a CL mimic, shown in FIG. 7b.
Figure 7B:
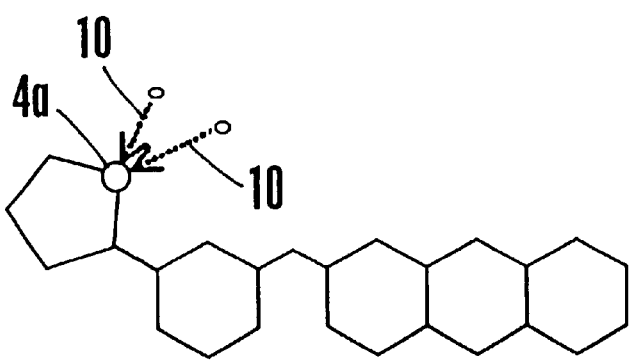
FIG. 7 illustrates the identification of the proximal atom in the CL mimic using 3D-HSQC NOESY with TROSY.

In the second stage, NMR spectra can be collected for the enzyme in complex with a CL mimic. For example, a TROSY implementation of the 3D [$^1$H—$^{15}$N] HSQC-NOESY is illustrated in FIG. 7. The third dimension, labeled "all proton chemical shifts," identifies protons—especially on the CL mimic—that receive an NOE-type perturbation from the protons identified in the first stage. The identity of these NOE-perturbed protons on the CL mimic are easily established based on chemical shift values, since all protons on the CL mimic can be assigned by standard methods well known in the art (P. L. Rinalidi, *Two Dimensional NMR Spectroscopy: Applications for Chemists and Biochemists*, pages 841–872 (Croasmun and Carlson, eds.), VCH Pubs, New York (1994)). Isotope filtering can also be used in this third dimension to select only those protons not attached to $^{15}$N. These NOE-perturbed protons on the CL mimic and other atoms in this region represent the optimal positions for variation in constructing a bi-ligand library. Significantly, the optimal position has been identified without having previously determined the complete assignments or structure for the enzyme.

It may be necessary to identify which cross peaks in the enzyme-CL mimic complex correspond to the interface region protons identified in the first stage. This can beachieved by titrating the CL mimic onto the dehydrogenase and monitoring how the cross peak changes for the previously identified proton. Again, such experiments are not necessary if the cross peaks of interest can be identified by other means.

In summary, to facilitate the catalysis of an enzyme, an atom of the reactive region of a bound common ligand will be proximal to the SL site and the intervening interface region. The reactive region can then be used to identify proximal atoms in the interface region. In turn, by virtue of the proximity between the interface region and the CL site, the interface region can be used to identify proximal atoms in a bound common ligand mimic. Such proximal atoms will be nearest to the SL site and provide a basis for building bi-ligands that can bind to both the CL site and the SL site. As a corollary, the method can identify, by elimination, those atoms in the CL mimic that are too distant from the SL site to serve as useful points of variation.

In an alternate embodiment, the first stage can be performed by binding an SL to the SL site of the enzyme; perturbing the nucleus of an atom of the SL corresponding to an SL reactive region, and identifying an NMR cross-peak corresponding to the nucleus of an atom that is perturbed by the perturbation of the nucleus of the atom of the SL reactive region, thereby identifying an atom of the interface region. The second stage can be performed by binding an SL mimic to the SL site, perturbing the nucleus of the interface atom previously identified, and identifying an NMR cross-peak corresponding to the nucleus of an atom of the SL mimic that is perturbed by the perturbation of the nucleus of the interface atom, thereby identifying an atom of the SL mimic that is proximal to the interface region.

Thus, the following is a generalized embodiment of the invention for identifying an atom of a first ligand mimic that is proximal to an interface region. A given enzyme can bind a first ligand (L1) or a first ligand mimic (L1 mimic) at a first ligand site (L1 site) and can bind a second ligand (L2) at an adjacent second ligand site (L2 site). The interface region can be defined as the atoms of the enzyme between the L1 site and L2 site, but also includes atoms of L2 if bound to the enzyme. An L1 reactive region is defined as the reactive atom of L1, as well as L1 atoms immediately adjacent to the reactive atom or L1 atoms immediately adjacent to L2. The first stage involves identifying an atom of the interface region, by binding an L1 to the L1 site of the enzyme, perturbing the nucleus of an atom of the L1 reactive region; and identifying an NMR cross-peak corresponding to the nucleus of an atom that is perturbed by the perturbation of the nucleus of the atom of the L1 reactive region, thereby identifying an atom of the interface region. The second stage involves identifying an atom in the L1 mimic that is proximal to the interface region, by binding an L1 mimic to the L1 site; perturbing the nucleus of the interface atom previously identified in the first stage; and identifying an NMR cross-peak corresponding to the nucleus of an atom of the L1 mimic that is perturbed by the perturbation of the nucleus of the interface atom, thereby identifying an atom of the L1 mimic that is proximal to the interface region.

It should be noted that CL mimics may bind to different positions within a CL site. For example, a particular CL mimic 4 may bind relatively close to the interface region, as shown in FIG. 3a, while another CL mimic 5 may bind distally, as shown in FIG. 3c. By identifying atoms proximal to the interface region, the method can therefore be used to screen for CL mimics that can bind proximally to the interface region. CL mimics like 5 that can bind distally may not contain atoms sufficiently close to the interface region to be useful for generating bi-ligand libraries.

Because the method uses. NMR methods to provide structural information to engineer a bi-ligand library, the method can be termed Nuclear Magnetic Resonance-Structure Oriented Library Valency Engineering or NMR-SOLVE$^{SM}$. Without NMR-SOLVE$^{SM}$, a combinatorial library based on the CL mimic would involve variation at potentially every point on the CL mimic. With NMR-SOLVE$^{SM}$, the library can be focused at the optimal point of variation, representing a significant savings in drug discovery time.

Thus, the present invention also provides a method for generating a focused combinatorial library of bi-ligand compounds that can simultaneously bind to a CL site and an SL site of an enzyme. The term "combinatorial library" herein means an intentionally created set of differing molecules prepared by taking a base structure and, in parallel reactions, adding different substituent groups to points on the base structure, resulting in the parallel synthesis of compounds that are variations on the core structure. By taking the products as core structures in a succeeding set of parallel reactions, further variant compounds can be generated, resulting in a diversity of related compounds. As a result of the combinatorial process, the products are generally prepared in essentially equimolar quantities, considering of course the different efficiencies of the individual synthetic reactions. Not included within this definition are multiple isomeric and chiral products and undesired by-products resulting from a single reaction scheme. Also not included are intentional or accidental mixtures of originally pure compounds not arising out of the combinatorial synthetic process.

A number of formats for generating combinatorial libraries are well known in the art, for example soluble libraries, compounds attached to resin beads, silica chips or other solid supports. As an example, the "split resin approach" may be used, as described in U.S. Pat. No. 5,010,175 to Rutter and in Gallop et al., *J. Med. Chem.*, 37:1233–1251 (1994).

The term "substituent group" herein means any chemical compound or functional group that can be synthetically attached to abase structure. Examples of substituent groups suitable for addition to a base structure include halo, hydroxy and protected hydroxyls, cyano, nitro, $C_1$ to $C_6$ alkyls, $C_2$ to $C_7$ alkenyls, $C_2$ to $C_7$ alkynyls, $C_7$ to $C_6$ substituted alkyls, $C_2$ to $C_7$ substituted alkenyls, $C_2$ to $C_7$ substituted alkynyls, $C_1$ to $C_7$ alkoxys, $C_1$ to $C_7$ acyloxys, $C_1$ to $C_7$ acyls, $C_3$ to $C_7$ cycloalkyls, $C_3$ to $C_7$ substituted cycloalkyls, $C_5$ to $C_7$ cycloalkenyls, $C_5$ to $C_7$ substituted cycloalkenyls, a heterocyclic ring, $C_7$ to $C_{12}$ phenylalkyls, $C_7$ to $C_{12}$ substituted phenylalkyls, phenyl and substituted phenyls, naphthyl and substituted naphthyls, cyclic $C_2$ to $C_7$ alkylenes, substituted cyclic $C_2$ to $C_7$ alkylenes, cyclic $C_2$ to $C_7$ heteroalkylenes, substituted cyclic $C_2$ to $C_7$ heteroalkylenes, carboxyl and protected carboxyls, hydroxymethyl and protected hydroxymethyls, amino and protected aminos, (monosubstituted)amino and protected (monosubstituted)aminos, (disubstituted)aminos, carboxamide and protected carboxamides, $C_1$ to $C_4$ alkylthios, $C_1$ to $C_4$ alkylsulfonyls, $C_1$ to $C_4$ alkylsulfoxides, phenylthio and substituted phenylthios, phenylsulfoxide and substituted phenylsulfoxides or phenylsulfonyl and substituted phenylsulfonyls. As discussed below, substituent groups can also include compounds that are ligands to enzymes such as a SL or SL mimics, as well as linkers.

Under the method of the invention, the libraries are generated by first performing the methods disclosed above to identify an optimal CL mimic and a CL mimic atom that is proximal to the interface region. In FIG. 4, for example, the proximal atom 4a has been identified. Then, compounds are synthesized by modifying the CL mimic at the proximal atom by attaching substituent groups.

For example, a focused combinatorial library 6 has been generated by using the proximal atom 4a as a point of variation on the CL mimic core structure 4. The library contains several compounds 6a–6d, each having a substituent group added at the proximal atom 4a. Thus, the term "focused" herein means a combinatorial library where substituent groups are added to preselected points on the core structure. In contrast, an unfocused combinatorial library 7 could begin with a non-optimal CL mimic 5 or begin with the same CL mimic 4 as a core structure, but the addition of substituent groups could occur at any point on the base structure, for example at an atom 4b distant from the SL site, leading to a substantially greater number of potentially ineffective bi-ligand compounds to be screened.

Because the invention is directed to combinatorial libraries of bi-ligand compounds, a particularly useful substituent group includes a chemical moiety that can bind to the SL site of the enzyme. The selection of such a moiety depends on the enzyme of interest, of course, but the substituent group can be an SL or SL mimic of an enzyme attached to the core, structure of the CL mimic, allowing the resulting compound to bind to both the SL and CL sites of the enzyme.

In some enzymes, the SL and CL sites can be a short distance apart, for example 2 Å. Nevertheless, when seeking a compound having moieties that can bind at both the SL and CL sites, it can be useful to incorporate a linker into the substituent group to span the distance between the two sites. The term "linker" herein means any chemical group or portion of a molecule used to physically connect one moiety to another moiety. For example in FIG. 4b, a linker 9 can connect an SL-site-binding moiety 8 to a CL mimic core structure 4 while maintaining the two moieties at a distance, allowing the compound 6c to bind the enzyme 1 tightly at both the SL site 1a and the CL site 1b. Thus, a linker can also provide positioning and orientation of the two moieties to optimize their binding to their respective binding sites.

Because the resulting library of compounds can bind to both sites of the enzyme, they can be described as "bi-ligands." The term "bi-ligand" herein means any molecule having at least two moieties where either moiety can bind to an enzyme independently or both moieties can bind to the same enzyme simultaneously. In such a bi-ligand, one moiety can be a CL or CL mimic. Similarly, the other moiety can be a SL or SL mimic. Thus, the invention also provides a combinatorial library of bi-ligand compounds obtained by the method of the invention for generating focused libraries. Such a library can contain at least 2, 5, 10, 15, 20 or 50 bi-ligand compounds. It can also contain 100, 200, 500, 1000 or even up to 10,000 or 100,000 bi-ligand compounds.

As a result of their ability to bind at multiple sites on an enzyme, the bi-ligand compounds in the libraries can have high affinities to the enzyme. Even if two individual moieties have relatively low binding affinities, the combination of the two ligands in a single bi-ligand compound can have a synergistically higher binding affinity (Radzicka & Wolfenden, "Transition State and Multisubstrate Inhibitors," *Methods in Enzymology* 249:284–303 (1995)). As an example, where two weakly binding ligands having binding affinities of 17 mM and 0.02 mM were linked, the resulting compound had a much higher binding affinity of 15 nM (Hajduk et al., "Discovery of Potent Nonpeptide Inhibitors of Stromelysin using SAR by NMR," *J. Am. Chem. Soc.* 119:5818–5827 (1997)). Accordingly, such bi-ligand compounds can be screened for their affinity to the enzyme or to other enzymes in the gene family.

Another advantage of these bi-ligand libraries is that the CL mimic can provide a certain baseline affinity for other members of the gene family. Further addition of a specificity ligand or SL mimic can provide additional affinity to other particular members. Thus, the library can be a rich source of specific bi-ligand inhibitors for multiple-members of a gene family.

Thus, the present invention further provides a method for screening libraries of bi-ligand compounds. After generating a combinatorial library of bi-ligand compounds as disclosed above, the binding of the compounds to the enzyme is measured. Individual compounds are then identified having greater binding than the CL mimic. Binding assays for enzymes and ligands are well known in the art and can be selected based on the particular enzyme and ligands being used.

Individual bi-ligand compounds identified by this screening method are also encompassed within the invention. In particular, such compounds can be screened that increase or decrease the activity of the enzyme. Moreover, such compounds can have extremely high binding affinities, having binding affinities of 100, 200, 1000, 5000 or even 10,000 times greater than the CL mimic's binding affinity. In addition to screening the bi-ligand compounds for affinity to the enzyme, it can be screened as an inhibitor for other members of the gene family. Binding to particular enzymes can also be particularly high when compared to other members of the gene family, so that the compound's binding affinity can be at least 50, 100, 200, 500, or 1000 times greater to the individual enzyme than to another enzyme in the same gene family. This specificity is provided by the binding interactions with the specificity ligands or SL mimics, since the common ligand can bind with similar affinity to multiple members of gene family.

Once high affinity bi-ligand compounds are identified, their binding to the enzyme at both CL and SL sites may be verified by the NMR methods disclosed above.

EXAMPLE 1

NMR-SOLVE[SM] of DHPR From *Mycobacterium Tuberculosis*

The following example illustrates the NMR-SOLVE[SM] method for identifying an optimal CL mimic and an atom of a CL mimic that is proximal to the interface region of an enzyme.

The enzyme dihydrodipicolinate reductase (DHPR) from *Mycobacterium tuberculosis* is selected because it plays a key role in the synthesis of the cell wall, and is vital for the survival of Mycobacterium (Pavelka and Jacobs, "Biosynthesis of Diaminopimelate, the Precursor of Lysine and a Component of Peptidoglycan, is an Essential Function of *Mycobacterium smegmatis*," *J. Bacteriol.* 178:6496–6507 (1996)).

Tuberculosis is a desirable biological target for drug design, since the genome has recently been made available, providing a rich source of new drug targets (Cole et al., "Deciphering the Biology of *Mycobacterium tuberculosis* from the Complete Genome Sequence," *Nature* 393:537–544 (1998)). Moreover, tuberculosis is the leading cause of death from infectious disease in adults (Dolin et al., "Global Tuberculosis Incidence and Mortality During 1990–2000," *Bull. WHO* 72:213–220 (1994)). Furthermore, tuberculosis is showing a resurgence in developing nations with increasing reports of drug resistant strains (Snider et al., "Global Burden of Tuberculosis," pages 3–11, in B. R. Bloom (ed.), *Tuberculosis: Pathogenesis, Protection, and Control*, ASM Press, Wash. D.C. (1994)).

A. Preparation of Uniformly $^{15}$N- and $^{13}$C-Labeled DHPR, With Deuterium in Non-exchangeable Positions Genomic DNA from *Mycobacterium tuberculosis* is prepared with standard methods (Sambrook et al., *Molecular Cloning: A Laboratory Manual*, Cold Spring Harbor Laboratory, Cold Spring Harbor N.Y. (2nd ed. 1989)). The DHPR gene is cloned using oligonucleotide primers complementary to the ends of the gene from the open reading frame sequence (Pavelka et al., "Cloning of the dapB Gene, Encoding Dihydrodipicolinate Reductase, from *Mycobacterium tuberculosis*," *J. Bacteriol.* 179:2777–2782 (1997) (Accession number U66101)). Standard PCR reactions are used with the GENEAMP PCR kit from Perkin Elmer (Norwalk Conn.).

The resulting fragment is cloned into both the PGEX (Pharmacia: Piscataway N.J.) and pET41 (Novagen: Madison Wis.) vectors, using manufacturer's instructions, with appropriate restriction enzymes for the respective vectors. The plasmid/gene constructs are then transformed into commercially available competent *E. coli* BL21 (DE3)pLysS strains (Invitrogen: Carlsbad Calif.), according to the manufacturer's instructions. The following expression is performed on a trial basis with each vector to empirically select for optimal expression yields.

*E. coli* containing the expression construct is adapted to grow in 100% D$_2$O using standard methods and glycerol stocks are prepared (Venters et al., "High-level $^2$H/$^{13}$C/$^{15}$N Labeling of Proteins for NMR Studies," *J. Biomol. NMR* 5:339–344 (1995)). Expression is performed in defined media of 3 g/L sodium [1,2-$^{13}$C2, 99%] acetate or 2 g/L [U—$^{13}$C6, 99%] D-glucose as the sole carbon source and 1 g/L [$^{15}$N, 99%] ammonium chloride or [$^{15}$N, 99%] ammonium sulfate as the sole nitrogen source. All stable isotopes are from Cambridge Isotopes, Inc. (Andover Mass.) and Isotec, Inc. (Miamisburg Ohio). The media also contains a modified M9 salt mixture: 44 mM Na$_2$HPO$_4$, 22 mM KH$_2$PO$_4$, 9 nM NaCl, 1 mM MgSO$_4$, 0.1 µM CaCl$_2$, 0.02 µM FeCl$_3$ and basal medium Eagle vitamin mix (Gibco-BRL), with the appropriate antibiotic for the expression vector, such as 50 µg/mL carbenecillin). All reagents are prepared in D$_2$O.

This media is inoculated at 37° C. from either a glycerol stock or from a freshly plated colony. When the absorbance at 600 nm reaches 0.4–0.8, DHPR production is induced by adding isopropyl-β-D-thiogalactopyranoside to a final concentration of 500 µM and incubated for 12 to 18 hours. Cells are harvested by centrifugation at 5000 rpm for 20 min at 5° C., then lysed with sonication.

The protein is purified on a glutathione affinity column using the manufacturer's instructions, which includes removal of the glutathione-S-transferase enzyme with thrombin cleavage. The protein is also purified with FPLC anion- or cation-exchange chromatography using standard procedures (Pharmacia: Piscataway N.J.). To perform experiments relying on $^1$H—$^{15}$N correlations, the solvent-exposed deuterated amide positions are exchanged with protons by incubating the protein at pH 7.5 at room temperature for 2 to 24 hours, then exchanging into a lower pH buffer (such as 20 mM phosphate buffer at pH 6.0) at 5° C. using a PD10 gel filtration column (Pharmacia) or CENTRICON 10 filter (Millipore: Bedford Mass.). Although not all amides are exchanged, the solvent-exposed amides do exchanges and the unfilled active sites are sufficiently exposed to allow exchange. Avoiding complete exchange has the advantage of simplifying the 3D NMR spectra. Protein for NMR experiments is present at 0.5–5 mM, although lower concentrations can be used with a cryoprobe (Bruker: Billerica Mass.).

B. Identification of CL Mimics

The common ligand of DHPR is NADH or AND$^+$. CL mimics are identified by displacement experiments. Such displacement is measured using standard steady-state kinetic analysis where the concentration of NADH is varied near its Km concentration in the presence of a single, fixed concentration of the other substrate, dihydrodipicolinate (Reddy et al., "Expression, Purification, and Characterization of *Eschericia coli* Dihydrodipicolinate Reductase," *Biochemistry* 34:3492–3501 (1995); Reddy et al., "Interaction of Pyridine Nucleotide Substrates with *Eschericia coli* Dihydrodipicolinate Reductase: Thermodynamic and Structural Analysis of Binary Complexes," *Biochemistry* 35:13294–13302 (1996)). This is repeated in the presence of several concentrations of a potential CL mimic. If Lineweaver-Burk plots (1/velocity versus 1/[NADH]) are prepared at the different concentrations of CL mimic inhibitor, according to the equation for a competitive inhibitor, an intersecting pattern will be obtained if the CL mimic binds in the NADH site (Cleland, W. W., *Methods Enzymol.* 63:103–138 (1979)).

It is also possible to identify CL mimics in a displacement assay that is generally useful for multiple members of a gene family. A fluorescently labeled CL mimic is displaced by a candidate CL mimic and the displacement is detected with fluorescence polarization (Burke et al., *Phage Display of Peptides and Proteins*, Academic Press, New York N.Y. (1996)).

The above methods disclose how CL mimic candidates are experimentally validated as binding at the CL site. Molecules to be screened in such an assay can be synthesized or purchased from chemical supply houses. Commercially available molecules are preferably chosen according to some pre-selection criteria, such as by identifying those molecules present in a database of commercially available molecules (Asinex: Moscow, Russia) that have similar shape and electronic properties to a target structure such as the known common ligand (NADH) or a structurally characterized CL mimic (such as cibacron blue).

THREEDOM software was used to search for matches against a target structure. THREEDOM employs a gnomonic projection algorithm for shape-matching a target structure in an INTERCHEM format 3D structure coordinate file against a database of multiple structure/coordinates (Doucet and Weber, *Computer-Aided Molecular Design: Theory and Applications*, Academic Press, San Diego Calif. (1996)). The target used to search the ASINEX database was cibacron blue. Coordinates were obtained from the published 3D structure (Li et al., "The Three-dimensional Structure of AND(P)H:quinone Reductase, a Flavoprotein Involved in Cancer Chemoprotection and Chemotherapy: Mechanism of the Two-electron Reduction," *Proc. Natl. Acad. Sci. USA* 92:8846–8850 (1995)). The database was created by converting an SD format file of structures from ASINEX to INTERCHEM format coordinates using the batch2to3 program. The target is compared against each structure in the database in multiple orientations to generate a matching score. Out of 37,926 structures searched, the 750 best matching scores were selected. From these 750 structures, 250 are selected and purchased based on objective criteria such as likely favorable binding interactions, pharmacophore properties, synthetic accessibility and likely pharmacokinetic, toxicological, adsorption and metabolic properties.

C. NMR-based Identification of Protein Interface Atoms

NMR experiments are performed on a Bruker 700 MHZ NMR spectrometer equipped with a $^1H/^{13}C/^{15}N$ triple resonance probe able to simultaneously perform broadband $^2H$ decoupling and $^2H$ locking. Triple resonance experiments are performed, and data are processed with standard methodology (Cavanagh et al., *Protein NMR Spectroscopy: Principles and Practice*, Academic Press, New York (1996)).

A 1 mM solution of labeled ($^2H$, $^{13}C$ and $^{15}N$) DHPR is prepared in 95% $H_2O$/5% $D_2O$, pH 6.0 and kept at 5° C. All of the NMR experiments are performed in the presence of a stoichiometric excess of 2,6-pyridinedicarboxylate. The compound 2,6-pyridinedicarboxylate is an analog of dihydrodipicolinate, the other DHPR substrate. The compound is present in excess to produce a dead-end complex that forces the enzyme into a closed conformation so that SL-binding and CL-binding domains are proximal (Scapin et al., "Three-Dimensional Structure of *Eschericia coli* Dihydrodipicolinate Reductase in Complex with NADH and the Inhibitor 2,6-Pyridinedicarboxylate," *Biochemistry* 36:15081–15088 (1997); Wang et al., "Hydrogen/Electrospray Ionization Mass Spectrometry Studies of Substrate and Inhibitor Binding and Conformation Changes of *Escherichia coli* Dihydrodipicolinate Reductase, *Biochemistry* 36:3755–3759 (1997)).

3D HNCO and 3D HNCA data are collected for the binary complexes of enzyme bound with 2,6-pyridinedicarboxylate, and for ternary complexes further binding NADH or NADD. In addition, 3D HNCA spectra are collected at multiple concentrations of NADH to identify those cross peaks in the binary complex corresponding to those in the ternary complex that are most affected by the H to D substitution between NADH and NADD. NADD [4R position labeled] is prepared enzymatically from NAD and perdeutero ethanol using alcohol dehydrogenase (Sem and Kasper, "Geometric Relationship between the Nicotinamide and Isoalloxazine Rings in NADPH-Cytochrome P-450 Oxidoreductase: Implications for the Classification of Evolutionarily and Functionally Related Flavoproteins," *Biochemistry* 31: 3391–3398 (1992)).

The experiments performed with NADD are repeated with the other NADH analog, nicotinic acid adenine dinucleotide (reduced), which has the carboxamide group replaced with acarboxylic acid. The reduced form is prepared enzymatically from the oxidized form of nicotinic acid adenine dinucleotide using alcohol dehydrogenase and unlabeled ethanol, as disclosed above. Although multiple NAD (P)(H) analogs are available for these perturbation studies, those chosen provide adequate chemical shift perturbations for this study (Everse et al. *The Pyridine Nucleotide Coenzymes*, Academic Press, New York N.Y. (1982)). Because the changes are made to the portion of the NADH molecule known to be closest to the SL site, the cross peaks that shift as a result of the chemical changes to NADH are therefore determined to be at the interface region between the two binding sites.

HNCO and HNCA experiments (Kay et al., *J. Magn. Reson.* 89:496–514 (1990); Grzesiek and Bax, *J. Magn. Reson.* 96:432–440(1992)) were performed as the TROSY implementation to produce narrower line-widths for the $^{15}N$—$^1H$ correlations (Salzmann et al., "TROSY in Triple Resonance Experiments: New Perspectives for Sequential NMR Assignment of Large Proteins," *Proc. Natl. Acad. Sci. USA* 95:13585–13590 (1998); Salzman et al., "TROSY-type Triple-Resonance Experiments for Sequential NMR Assignments of Large Proteins, *J. Am. Chem. Soc.* 121:844848 (1999)). Deuterium labeling and decoupling is also included to produce narrower line widths, particularly for $^{13}C$ resonances (Yamazakiet al., "A Suite of Triple Resonance NMR Experiments for the Backbone Assignments of $^{15}N$, $^{13}C$, $^2H$ Labeled Proteins with High Sensitivity," *J. Am. Chem. Soc.* 116:11655–11666 (1994)). Spectra are processed with both Felix (MST: San Diego Calif.) and NMRPipe software (NIH: Bethesda, Md.) (Delaglio et al., "NMRPipe: a Multidimensional Spectral Processing System Based on UNIX Pipes" *J. Biomol. NMR* 6:277,293 (1995)).

D. NMR-based Identification of Proximal CL Mimics and Proximal Atoms on CL Mimics NMR experiments are performed as in the first paragraph of section C. 3D HNCA data are collected at multiple concentrations of each CL mimic identified in section B as a competitive inhibitor against NADH. At the highest concentration of the CL mimic, two types of NOESY experiments are performed. The first is a TROSY implementation of the 3D [$^1H$—$^{15}N$] HSQC-NOESY. Since there is significant cross-peak overlap in the 3D experiment, 4D versions of the HNCA and HNCO experiments are also performed (Kay et al., "Four-Dimensional Heteronuclear Triple-Resonance NMR Spectroscopy of Interleukin-1b/in Solution," *Science* 249: 411–414 (1990)). The 4th dimension is for NOEs from the $^{13}N$-attached protons to any other proton. The NOEs of interest are those from the perturbed cross-peaks identified in section C to any protons on the CL mimic being studied. These protons therefore represent optimal positions on the CL mimic for library expansion by attaching linkers.

E. Linker Attachment and Validation

Once a linker is synthetically attached to the CL mimic according to atoms of interest identified in section D, NMR experiments are performed on the DHPR ternary complex with 2,6-pyridinedicarboxylate and the modified CL mimic. NMR experiments are performed as in the first paragraph of section C. 3D HNCA data are collected at multiple concentrations of the modified CL mimic (with linker attached), as disclosed in section D. These cross-peak perturbations are compared with those observed in previous (section D) experiments with the original unmodified CL mimic. From these data it is established that the modified CL mimic contacts the same binding site atoms in both complexes. Additional cross-peak perturbations due to attachment of a linker should also correspond to some of the interface atoms identified in section C.

In addition to NMR experiments, steady-state inhibition experiments are performed as disclosed in section B to establish that the modified CL mimic is still a competitive inhibitor against NADH, and to determine the dissociation constant with DHPR to establish that adding the linker does not significantly disrupt the strength of the binding interactions with DHPR.

EXAMPLE II

NMR-SOLVE[SM] of DHPR From *Escherichia coli*

Given the similarity of DHPR protein sequences in *Mycobacterium tuberculosis* and *Escherichia coli*, and the higher levels of expression in *E coli*, DHPR from *E. coli* was used in the following example.

The common ligand for DHPR was NADH (FIG. 9b) and the specificity ligand was dihydrodipicolinate. An analog of NADH, AcNADH (FIG. 9c) was used for chemical perturbation experiments. Similarly, an analog of specificity ligand dihydrodipicolinate was used: SL analog 2,6-pyridinedicarboxylate (2,6-PDC) (FIG. 9a).

A. Preparation of Uniformly $^{15}$N-Labeled DHPR, With Deuterium in Non-exchangeable Positions, Except Threonines, Which Were $^{13}$CH$_3$-Labeled 1. Expression and Isotopic Enrichment of DHPR DHPR was prepared that was uniformly enriched in $^2$H and $^{15}$N and containing $^1$H/$^{15}$N/$^{13}$C-labeled threonine residues. 2 mL LB media with 100 mg/mL carbenicillin was inoculated aseptically with 20 mL of a glycerol stock of *E coli* containing the pET11a+/DHPR expression construct (Reddy et al., supra). This culture was grown to OD$_{600}$ 0.4–0.5 at 37° C. Cells were then conditioned to grow on deuterated media. The first step was a 50-fold dilution of the LB culture into 2 mL of 90% D$_2$O from Cambridge Isotope Laboratories or Isotec, Inc in minimal media containing 5 g/L D-glucose, 2 g/L NH$_4$Cl, 10.725 g/L Na$_2$HPO$_4$.H$_2$O, 4.5 g/L KH$_2$PO$_4$, 0.75 g/L NaCl, 2 mM MgSO$_4$ and 2 mL (1×) of the following trace metal and nutrient solution: 2 mg/mL CaCl$_2$, 2 mg/mL ZnSO$_4$.7H$_2$O, 15 mg/mL thiamine, 10 mg/mL niacinamide, 1 mg/mL biotin, 1 mg/mL choline chloride, 1 mg/mL pantotenic acid, 1 mg/mL pyridoxine, 1 mg/mL folic acid, 10.8 mg/mL FeCl$_3$.6H$_2$O, 0.7 mg/mL Na$_2$MoO$_4$.2H$_2$O, 0.8 mg/mL CuSO$_4$.5H$_2$O and 0.2 mg/mL H$_3$BO$_3$.

This culture was grown to OD$_{600}$ 0.3–0.4 at 37° C. and then diluted 40-fold into 5 mL of 100% D$_2$O M9 minimal media, which was identical to the media above except the D-glucose was uniformly $^2$H-enriched (Martek Biosciences Corp.: Columbia Md.) and the ammonium chloride was uniformly $^{15}$N-enriched (Martek). This 5 mL culture was grown overnight and then used to inoculate 100 mL of the same media. The 100 mL culture was grown at 37° C. in a 1 L baffled shaker flask for 16 hours to a final OD$_{600}$ of 4.5–5.0.

Protein expression was then carried out on a 1 L scale in a BIOFLOW 3000 fermentor (New England Biolabs: Beverly Mass.). The pH of the culture was monitored via a gel-filled pH probe and maintained at pH 7.0 by the automated feeding of 0.1N NaOD. The culture was aerated by continuous sparging of dried air at a flow rate of 5 L/minute. The temperature was maintained at 37° C. via a recirculating chiller, and the dissolved oxygen level was monitored via a D.O. probe.

The 100 mL shaker flask culture was used to inoculate 1 L basal fermentation media containing 2 gm/L $^2$H-D-glucose, 0.8 g/L $^{15}$NH$_4$Cl and 0.5× of the trace metal and vitamin mix. The culture was grown until the pH feed was inactive and the dissolved oxygen level began to rise, at which time a batch-feed solution was added, consisting of 3 gm/L $^2$H-D-glucose, 1.2 gm/L $^{15}$NH$_4$Cl, 0.5× of the trace metal and vitamin mix and 100 mg U—$^2$H/$^{15}$N/$^{13}$C-labeled threonine (Cambridge). After a re-equilibration period of 10 to 15 minutes, protein expression was induced by adding 2 mM IPTG. The induction phase was carried out until the pH feed was inactive and the pH value began to rise with final cell densities ranging from OD$_{600}$ 4–5. The cells were then pelleted at 5000×g, 4° C. for 10 minutes in four 250 mL fractions and frozen at −80° C.

2. Purification

The cell pellet from one of the fractions was resuspended in 250 mL ice-cold lysis buffer consisting of 50 mM Tris pH 7.5, 100 mM NaCl, 1 mM EDTA, and 1 mL protease inhibitor cocktail. The resuspended cell pellet was, homogenized for 3 minutes. The homogenized, resuspended cells were then lysed by three passes at 18,000 PSI through a microfluidizer. The soluble fraction was separated from the insoluble cellular debris by centrifugation at 20,000×g, 4° C. for 45 minutes. The supernatant was then dialyzed against 2 L of 50 mM Tris pH 7.8, 1 mM EDTA for 4 hours and subsequently cleared by centrifugation at 20,000×g, 4° C. for 45 minutes.

The cleared, dialyzed soluble cellular fraction was then loaded on a 100 mL FAST FLOW Q-SEPHAROSE quaternary ammonium ion exchange column (Pharmacia), that had been equilibrated in 25 mM Tris pH 7.8, 1 mM EDTA. The column was washed extensively with equilibration buffer, and the protein eluted in 5 mL fractions with a 1 L 0–1 M NaCL gradient at a flow rate of 1 mL/minute. Eluted fractions were analyzed by SDS-PAGE. Fractions containing significant levels of DHPR were pooled and loaded in two fractions onto 50 mL FAST FLOW BLUE SEPHAROSE 6 dye-affinity column (Pharmacia), which had been equilibrated in 20 mM Tris pH 7.8, 1 mM EDTA. The column was washed with 2 column volumes of equilibration buffer and the protein was eluted with equilibration buffer containing 2M NaCl. Approximately 200 mg/L of >99% pure DHPR was obtained, representing a yield of about 150 mg/L.

The protein was $^{13}$CH$_3$-labeled at threonine positions so that NMR-observable atoms were present on the protein in addition to amides. Thus, NMR-SOLVE experiments could be performed that involved either backbone amides in $^1$H—H$^{15}$N correlation spectra or at methyl groups of threonines in $^1$H—$^{13}$C correlation spectra. Narrow line widths were obtained in $^1$H—$^{15}$N correlation spectra by using the TROSY pulse sequence (Salzman et al. (1998) supra; Salzman et al. (1999) supra; Wider and Wuethrich, "NMR spectroscopy of large molecules and multimolecular assemblies in solution" *Current Opinion in Structural Biology* 9:594–601 (1999)). In $^1$H—$^{13}$C correlation spectra, narrow line widths were obtained because of the fast rotation of methyl protons. Methyl protons have the added advantage of increased sensitivity because of the presence of three equivalent protons. Specific labeling of residues, such as threonines, has the advantage of simplifying 2D-NMR spectra.

B. Identification of CL Mimics

CL mimics for DHPR include NADH, NAD, NADPH or NADP. Mimics of NADH or NAD were obtained by screening for displacement of the natural common ligand with the enzyme lactate dehydrogenase (LDH). Such displacement was measured using standard steady-state kinetic analysis, where NADH was varied around its K$_m$ in the presence of a single fixed concentration of the other substrate, pyruvate (Zewe and Fromm, *Biochemistry* 4:782–792 (1965)). This was repeated in the presence of several concentrations of a potential CL mimic.

When Lineweaver-Burk plots (1/rate versus 1/[NADH]) were drawn at the different concentrations of CL mimic inhibitor, an intersecting pattern would be obtained if the CL mimic was binding in the NADH site, according to the equation for a competitive inhibitor (Cleland, supra). It was also possible to identify CL mimics in a generally useful (across a gene family) displacement assay: a fluorescently labeled CL mimic was displaced by a candidate CL mimic. The displacement was detected with fluorescence polarization. This can be performed in the same manner as with peptides (Burke et al., supra), but with CL mimics.

The method above describes how CL mimic candidates were experimentally validated for binding in the CL site. Molecules to be screened in such assays were synthesized or purchased from chemical supply houses. The candidates were pre-selected by computationally identifying molecules present in a database of commercially available molecules (ASINEX: Moscow, Russia) that had similar shape and electronic properties to either the known common ligand, NADH, or a structurally characterized CL mimic, such as cibacron blue.

THREEDOM software (Interprobe Chemical. Services: Glasgow, Scotland) was used to perform this search for matches against a target structure. THREEDOM employed a gnomonic projection algorithm (Doucet and Weber supra) for shape-matching a target structure in an Interchem-format 3D-structure coordinate file (Interprobe Chemical Services: Glasgow, Scotland) against a database of multiple structures/coordinates. The target used to search the ASINEX database was cibacron blue. Coordinates were obtained from the published 3D structure (Li et al. supra). The database was created by converting an SD format file of structures from ASINEX to Interchem format coordinates using the batch2to3 program (Interprobe Chemical Services).

The target was compared against each structure in the database in multiple orientations, and a matching score was generated for the optimal orientation and overlay. Out of 74,500 structures searched, the 1244 with best matching scores were selected and purchased. These compounds were screened in the above-mentioned steady-state inhibition assay with LDH. One of the inhibitors identified, designated as TTE0001.002.D2, is shown in FIG. 8a.

Figure 8B:
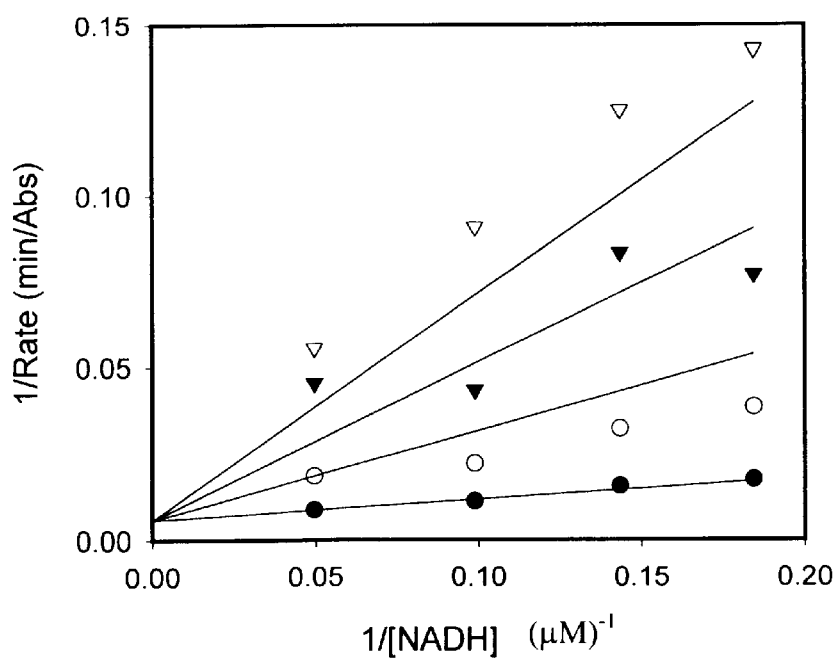
FIG. 8b shows a Lineweaver-Burk plot for the compound in competition with NADH for lactate dehydrogenase.

The inhibition profile for that compound is shown in FIG. 8b. The Lineweaver-Burk plot for the compound with lactate dehydrogenase was plotted showing 1/[NADH] $(\mu M)^{-1}$ on the horizontal axis versus 1/rate (min/Abs) on the vertical axis. Reactions were carried out in 0.1 M HEPES buffer pH 7.4, 2.5 mM pyruvate and 5 $\mu$g/mL LDH, with DMSO kept fixed at 3%. NADH was varied at 5.4, 7.0, 10.1, and 20.1 $\mu$M, and the compound was present at 0 (solid circles), 6.9 (open circles), 13.7 (closed triangles) and 20.6 $\mu$M (open triangles). Initial rates were measured by monitoring absorbance changes at 340 nm. The competitive inhibition pattern indicated that it bound in the NADH (common ligand) site with a dissociation constant of 2.1±0.4 $\mu$M.

C. NMR-based Identification of Protein Interface Atoms

NMR experiments were performed on a 700 MHZ NMR spectrometer (Bruker NMR: Fremont Calif.) equipped with a $^1$H/$^{13}$C/$^{15}$N triple resonance probe able to simultaneously perform broadband $^2$H decoupling and $^2$H locking. Multiple resonance experiments were performed. Data were processed with standard methodology (Cavanagh et al. supra). Most experiments were performed with about 1 mM DHPR samples at about pH 7.5, 25 mM Tris-d$_{11}$ buffer in 99% D$_2$O or in 95% H$_2$O/5% D$_2$O, with sample at 30° C. $^{13}$C—$^1$H correlation experiments were obtained via HMQC. magnetization transfer because it was more sensitive than HSQC for the particular samples. Adiabatic WURST $^{13}$C$^\beta$ decoupling was applied during the $^{13}$C t1 evolution time. A 5 ms WURST-10 adiabatic pulse shifted at 70 ppm was applied to decouple $^{13}$C$^\gamma$ from $^{13}$C$\beta$. Typically, 100*20.48 complex points were acquired with 16 to 32 scans per increment, with a total time between about 1 to 2 h per HMQC experiment. Typical 2D [$^1$H,$^1$H] NOESY were acquired with 256*2048 complex points and with mixing times between 100 ms and 500 ms. $^{13}$C$^\gamma$ decoupling during t1 evolution was achieved with a $^{13}$C 180 degree refocusing pulse. $^{13}$C decoupling during the acquisition was achieved with a GARP composite decoupling sequence. The measuring time for a 2D [$^1$H,$^1$H] NOESY varied from about 12 to 48 h.

Ligand characterization and structure elucidation was accomplished with standard 1D $^1$H and 1D $^{13}$C NMR, as well as 2D [$^1$H,$^1$H] COSY and, in some cases, 2D [$^1$H,$^1$H] ROESY. Frequently, NMR experiments were performed in the presence of 3 mM 2,6-pyridinedicarboxylate (2,6-PDC), to produce a dead-end complex that would force the enzyme into a closed conformation (Scapin et al. supra; Wang et al. supra). 2,6-pyridinedicarboxylate (FIG. 9a) was an analog of the other substrate, dihydrodipicolinate. Substrate and cofactor domains of dehydrogenases most frequently adopt a closed conformation where both domains are proximal and when both ligands are bound.

Figure 9C:
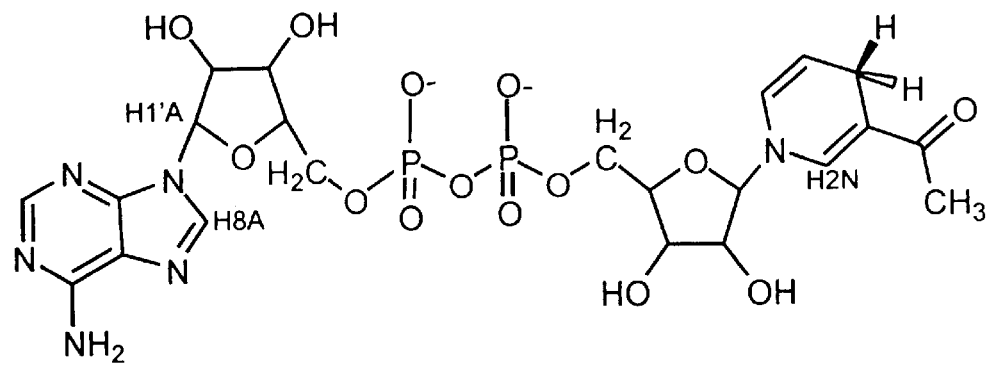

2D $^1$H—$^{13}$C HSQC data were collected for the enzyme without ligand bound (FIG. 10a), and for the binary complex with NADH (FIGS. 9b and 10b) or the binary complex with 3-acetylpyridine adenine dihucleotide (AcNADH) (FIGS. 9c and 10c). In addition, spectra were collected at multiple concentrations of NADH or AcNADH to identify cross peaks in the apo enzyme corresponding to the binary complex that were most affected by the amine-to-methyl substitution in going from NADH (FIGS. 9b and 10b) to AcNADH (FIGS. 9c and 10c).

Although multiple NAD(P)(H) analogs are available for these perturbation studies (Everse et al. supra), AcNADH provided adequate chemical shift perturbations for this study. The protein cross peaks that shifted as a result of the chemical changes to the NADH molecule were at the interface of the two binding sites, since the changes were made to a part of the NADH molecule known to be proximal to the specific binding site. Two protein cross-peaks were perturbed by the amide (FIG. 9b) to methyl (FIG. 9c) substitution on NADH, shown by comparing FIGS. 10b and 10c. Those effects were quantified in FIG. 11.

Figure 12:
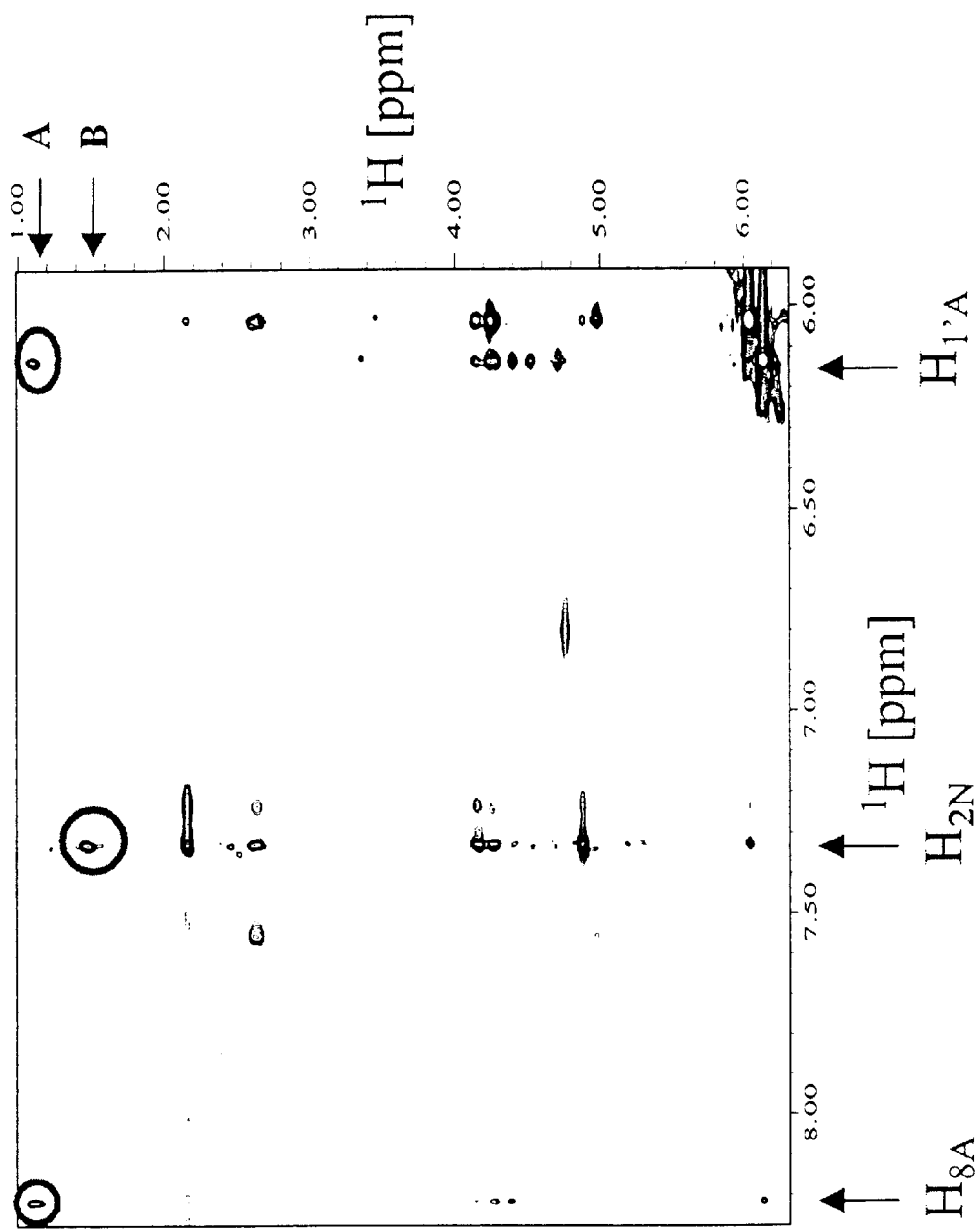

In addition to chemically perturbing the common ligand NADH and looking for an effect on protein, protons on AcNADH were also perturbed by irradiation, as in a standard 2D NOESY experiment (FIG. 12), and looking for effects on the protein in the form of an NOE, as indicated by a cross-peak between the AcNADH protons and protons on the protein corresponding to cross-peak #2 in FIGS. 9c and 10c.

In this case, because of the specific labeling of the protein, the protons on the protein were the methyl protons of threonines. The combination of these two experiments unambiguously identified cross-peak #2 as corresponding to atoms at the interface of the CL (NADH) site and SL site. Furthermore; perturbation by irradiation of the interface atoms on the other ligand, 2,6-PDC, also produced NOEs to cross-peak #2 in the ternary complex, further confirming its assignment as corresponding to an interface atom. It should be noted that the additional NOEs in FIG. 11 from the H8A and H1'A protons of AcNADH were to another threonine methyl that was in a part of the CL site, which was more remote from the interface region.

D. NMR-based Identification of Proximal CL Mimics and Proximal Atoms on CL Mimics CL mimic protons were first assigned based on 2D-COSY data before binding the CL mimic to the DHPR protein, and also in the presence of protein. NMR experiments were performed as in the first paragraph of section C. 2D $^1$H—$^{13}$C HMQC data were collected at multiple concentrations of the CL mimic identified in section B. At the highest concentration of the CL mimic, a 2D-NOESY experiment was carried out with a mixing time of 200 msec (FIG. 13). The NOEs of interest were from the perturbed interface cross-peak identified in section C to any protons on the CL mimic being studied. NOEs from the interface atom identified as cross-peak #2 matched only the H1 proton of the CL mimic TTE0001.002.D2. This confirmed the assignment of the H1 proton as an atom proximal to the interface region. As shown, NOEs are also observed from the interface atom identified as cross-peak #2 to bound SL analog 2,6-PDC. Also, perturbation of the interface atoms on the 2,6-PDC produced an NOE to the H1 proton of the CL mimic.

Thus, proton H1 represents the optimal region of the CL mimic TTE0001.002.D2 to attach a linker for bi-ligand library expansion, so that diversity elements can be geometrically directed into the SL site.

Each of the references and U.S. Patents cited above is hereby incorporated herein by reference.

Although the present invention has been exemplified by the disclosed embodiments, those skilled in the art will readily appreciate that the specific examples are provided to illustrate, not to limit, the invention. Thus, while bacterial enzymes have been presented for purposes of illustration, the methods of the invention may be readily applied to identifying drug candidates effective against enzymes involved in other diseases where inhibition of bi-ligand enzymes would be advantageous, for example cancer, cardiovascular disease and other microbial and viral infections such as HIV. It should therefore be understood that various modifications can be made without departing from the spirit of the invention. Accordingly, the invention is limited only by the following claims.

We claim:

1. A method for identifying an atom of a common ligand mimic that is proximal to an interface region of an enzyme;
   wherein the enzyme can bind a common ligand (CL) or a common ligand mimic (CL mimic) at a common ligand site (CL site) and can bind a specificity ligand (SL) at an adjacent specificity ligand site (SL site);
   wherein an interface region is defined as the atoms of the enzyme between the CL site and SL site, and atoms of an SL if bound to the enzyme;
   wherein the enzyme can catalyze a reaction involving the SL and a reactive atom of the CL;
   wherein a CL reactive region is defined as the reactive atom of the CL and CL atoms immediately adjacent to the reactive atom or CL atoms immediately adjacent to the SL;
   comprising the steps of
   (1) mixing a CL and CL mimic with said enzyme to establish an equilibrium of a CL-enzyme complex and CL mimic-enzyme complex;
   (2) irradiating a nucleus of an atom of the CL, whereby energy is transferred from the nucleus of the CL atom to the interface region;
   (3) observing a perturbation of the nucleus of an atom of a CL mimic, whereby energy is transferred from the interface region to said atom of the CL, mimic; and
   (4) identifying in a multidimensional NMR experiment an NMR cross-peak corresponding to a nucleus of the CL mimic perturbed in step (3), thereby identifying an atom of the CL mimic that is proximal to the interface region.

2. A method for identifying a second atom of a common ligand that is proximal to an interface region of an enzyme;
   wherein the enzyme can bind a common ligand (CL) at a common ligand site (CL site) and can bind a specificity ligand (SL) at an adjacent specificity ligand site (SL site);
   wherein an interface region is defined as the atoms of the enzyme between the CL site and SL site, and atoms of an SL, if bound to the enzyme;
   wherein the enzyme can catalyze a reaction involving the SL and a reactive atom of the CL; and
   wherein a CL reactive region is defined as the reactive atom of the CL and CL atoms immediately adjacent to the reactive atom or CL atoms immediately adjacent to the SL;
   comprising the steps of
   (a) identifying an atom of the interface region, comprising the steps of
      (1) binding a CL to the CL site of said enzyme;
      (2) irradiating a nucleus of a first atom of the CL reactive region; and
      (3) identifying in a multidimensional NMR experiment, an NMR cross-peak corresponding to a nucleus that is perturbed by the irradiation of the nucleus of the CL reactive region, thereby identifying an atom of the interface region; then
   (b) identifying a second atom in the CL that is proximal to the interface region, comprising the steps of
      (1) binding a CL to the CL site of said enzyme;
      (2) irradiating the nucleus of the interface atom identified in step (a); and
      (3) identifying in a multidimensional NMR experiment, an NMR cross-peak corresponding to a nucleus of the CL mimic that is perturbed by the irradiation of the interface nucleus, thereby identifying a second atom of the CL that is proximal to the interface region.

3. The method of claim 2, wherein the atom of the CL reactive region in step (a) (2) is the reactive atom of the CL.

4. The method of claim 2, wherein the atom of the reactive region in step (a) (2) is a CL atom immediately adjacent to the reactive atom.

5. The method of claim 2, wherein the atom of the reactive region in step (a) (2) is a CL atom immediately adjacent to the SL.

6. The method of claim 2, wherein the CL is geranyl-pyrophosphate.

7. The method of claim 2, wherein the CL is geranyl-pyrophosphate.

8. A method for identifying an atom of a specificity ligand mimic that is proximal to an interface region of an enzyme;
   wherein the enzyme can bind a specificity ligand (SL) or a specificity ligand mimic (SL mimic) at a specificity ligand site(&L :site) and can bind a common ligand (CL) at an adjacent common ligand site (CL site);
   wherein an interface region is defined as the atoms of the enzyme between the SL site and CL site, and atoms of a CL, if bound to the enzyme;
   wherein the enzyme can catalyze a reaction involving the CL and a reactive atom of the SL; and
   wherein a SL reactive region is defined as the reactive atom of the SL and SL atoms in immediately adjacent to the reactive atom or SL atoms immediately adjacent to the CL;
   comprising the steps of
   (a) identifying an atom of the interface region, comprising the steps of
      (1) binding a SL to the SL site of said enzyme;
      (2) irradiating a nucleus of an atom of the SL reactive region; and
      (3) identifying in a multidimensional NMR experiment, an NMR cross-peak corresponding to a nucleus that is perturbed by the irradiation of the nucleus of the SL reactive region, thereby identifying an atom of the interface region; then (b) identifying an atom in the SL mimic that is proximal to the interface region, comprising the steps of
(1) binding a SL mimic to the SL size of said enzyme;
(2) irradiating the nucleus of the interface atom identified in step (a); and
(3) identifying in a multidimensional NMR experiment, an NMR cross-peak corresponding to a nucleus of the SL mitt that is perturbed by the irradiation of the interface nucleus, thereby identifying an atom of the SL mimic that is proximal to the interface region.

9. The method of claim 8, wherein the atom of the interface region identified in step (a) is an atom of a CL bound to the enzyme.

10. The method of claim 8, wherein the atom of the SL reactive region in step (a) (2) is the reactive atom of the SL.

11. The method of claim 8, wherein the atom of the reactive region in step (a) (2) is an SL atom immediately adjacent to the reactive atom.

12. The method of claim 8, wherein the atom of the reactive region in step (a) (2) is a SL atom immediately adjacent to the CL.

13. The method of claim 2 or 8, wherein the enzyme has a monomer molecular weight greater than 20 kD.

14. The method of claim 13, wherein the enzyme has a monomer molecular weight greater than 35 kD.

15. The method of claim 2 or 8, wherein the enzyme has a complete molecular weight greater than 50 kD.

16. The method of claim 15, wherein the enzyme has a complete molecular weight greater than 100 kD.

17. The method of claim 2 or 8, wherein the enzyme is from a human pathogen.

18. The method of claim 2 or 8, wherein the enzyme is from bacteria.

19. The method of claim 2 or 8, wherein the enzyme is a dehydrogenase.

20. The method of claim 2 or 8, wherein the enzyme is a kinase.

21. The method of claim 2 or 8, wherein the atom of the interface region identified in step (a) is an atom of the enzyme.

22. The method of claim 2 or 8, wherein the atom of the interface region identified in step (a) is an atom of an SL bound to the enzyme.

23. The method of claim 2 or 8, wherein the CL is a cofactor.

24. The method of claim 23, wherein the CL is ubiquitin.

25. The method of claim 23, wherein the CL is SAM (S-adenosyl methionine).

26. The method of claim 23, wherein the cofactor contains a nucleotide.

27. The method of claim 26, wherein the CL is NAD+.

28. The method of claim 26, wherein the CL is NADH.

29. The method of claim 26, wherein the CL is NADP+.

30. The method of claim 26, wherein the CL is NADPH.

31. The method of claim 26, wherein the CL is ATP.

32. The method of claim 26, wherein the CL is ADP.

33. The method of claim 2 or 8, wherein the CL is farnesyl-pyrophosphate.

34. The method of claim 2 or 8, wherein the NMR cross-peak is identified by the cross-peak undergoing an intensity or shape change.

35. The method of claim 2 or 8, wherein the NMR cross-peak is identified by a relaxation effect.

36. The method of claim 2 or 8, wherein the NMR cross-peak is identified by the cross-peak undergoing a chemical shift change.

37. The method of claim 2 or 8, wherein an NMR cross-peak is identified using a multidimensional multinuclear method, wherein the transfer of magnetization to protons is only to or from amide protons.

38. The method of claim 2 or 8, wherein an NMR cross-peak is identified using a multidimensional multinuclear method, wherein the detectable atoms are the NH protons of protein at an amino acid selected from the group consisting of Asn, Gln, Arg and His.

39. The method of claim 2 or 8, wherein an NMR cross-peak is identified using a multidimensional multinuclear method, wherein the detectable atoms are the methyl protons of protein specifically $^{13}C$—$^{1}H_3$ labeled at an amino acid selected from the group consisting of Leu, Thr, Ile Val, Ala and Met.

40. The method of claim 2 or 8, wherein an NMR cross-peak is identified using a multidimensional multinuclear NMR method that includes a $^{1}H$—$^{15}N$ correlation.

41. The method of claim 40, wherein the NMR method is a $^{1}H$—$^{15}N$ correlation and nuclear Overhauser enhancement spectroscopy experiment.

42. The method of claim 2 or 8, wherein an NMR cross-peak is identified using a multidimensional multinuclear NMR method that includes a $^{1}H$—$^{13}C$ correlation.

43. The method of claim 42, wherein the NMR method is an HNCA experiment.

44. The method of claim 2 or 8, wherein an NMR cross-peak is identified using an NMR method that includes a $\{^{1}H,^{1}H\}$ NOESY step.

45. The method of claim 44, further comprising the step of introducing a third dimension for $^{15}N$ or $^{13}C$ chemical shift.

46. The method of claim 44, wherein a diagnostic $^{1}H$—$^{13}C$ or $^{1}H$—$^{15}N$ one bond coupling constant is obtained without decoupling to a heteroatom in one of the two dimensions.

47. The method of claim 44, further comprising the step of using 2D $^{13}C$—$^{1}H$ or $^{15}N$—$^{1}H$ HMQC or HSQC-$\{^{1}H,^{1}H\}$ NOESY.

48. The method of claim 2 or 8, wherein an NMR cross-peak is identified using an NMR experiment that uses transverse relaxation-optimized spectroscopy (TROSY), whereby narrow line widths are achieved.

49. The method of claim 2 or 8, wherein an NMR cross-peak is identified by narrowing spectral line width utilizing a method selected from the group consisting of deuterium labeling, decoupling, and combinations thereof.

50. The method of claim 49, wherein said narrowing spectral line width is accomplished by decoupling.

51. The method of claim 49, wherein said narrowing spectral line width is accomplished by deuterium labeling.

52. The method of claim 49, wherein said narrowing spectral line width is accomplished by deuterium labeling and decoupling.

53. The method of claim 2 or 8, wherein immediately adjacent is within 5 Ångstroms.

54. The method of claim 2 or 8, wherein immediately adjacent is within 4 Ångstroms.

55. A method for identifying an atom of a common ligand that is proximal to an interface region of an enzyme;
wherein the enzyme can bind a common ligand (CL) at a common ligand site (CL site) and can bind a specificity ligand (SL) at an adjacent specificity ligand site (SL site);

wherein an interface region is defined as the atoms of the enzyme between the CL site and SL site, and atoms of an SL, if bound to the enzyme;

wherein the enzyme can catalyze a reaction involving the SL and a reactive atom of the CL; and wherein a CL reactive region is defined as the reactive atom of the CL and CL atoms immediately adjacent to the reactive atom or CL atoms immediately adjacent to the SL;

comprising the steps of
  (a) identifying an atom of the interface region, comprising the steps of
    (1) binding a CL to the CL site of said enzyme, and then performing a multidimensional NMR experiment;
    (2) binding a chemically modified CL to the CL site of the enzyme, wherein the modification is to an atom of the CL reactive region, and then repeating the same NMR experiment;
    (3) comparing the spectra from steps (a) (1) and (a) (2) to identify an NMR cross-peak corresponding to a nucleus that is affected by the chemical modification, thereby identifying an atom of the interface region; then
  (b) identifying an atom in the CL that is proximal to the interface region, comprising the steps of
    (1) binding a CL to the CL site of said enzyme;
    (2) irradiating the nucleus of the interface atom identified in step (a); and
    (3) identifying in a multidimensional NMR experiment, an NMR cross-peak corresponding to a nucleus of the CL that is perturbed by the irradiation of the interface nucleus, thereby identifying an atom of the CL that is proximal to the interface region.

56. A method for identifying an atom of a specificity ligand mimic that is proximal to an interface region of an enzyme;

wherein the enzyme can bind a specificity ligand (SL) or a specificity ligand mimic (SL mimic) at a specificity ligand site (SL site) and can bind a common ligand (CL) at an adjacent common ligand site (CL site);

wherein an interface region is defined as the atoms of the enzyme between the SL site and CL site, and atoms of a CL, if bound to the enzyme;

wherein the enzyme can catalyze a reaction involving the CL and a reactive atom of the SL; and wherein a SL reactive region is defined as the reactive atom of the SL and SL atoms immediately adjacent to the reactive atom or SL atoms immediately adjacent to the CL;

comprising the steps of
  (a) identifying an atom of the interface region, comprising the steps of
    (1) binding a SL to the SL site of said enzyme, and then performing a multidimensional NMR experiment;
    (2) binding a chemically identified SL to the SL site of the enzyme, wherein the modification is to an atom of the SL reactive region, and then repeating the same NMR experiment;
    (3) comparing the spectra from steps (a) (1) and (a) (2) to identify an NMR cross-peak corresponding to a nucleus that is affected by the chemical modification, thereby identifying an atom of the interface region; then
  (b) identifying an atom in the SL mimic that is proximal to the interface region, comprising the steps of
    (1) binding a SL mimic to the SL site of said enzyme;
    (2) irradiating the nucleus of the interface atom identified in step (a); and
    (3) identifying in a multidimensional NMR experiment, an NMR cross-peak corresponding to a nucleus of the SL mimic that is perturbed by the irradiation of the interface nucleus, thereby identifying an atom of the SL mimic that is proximal to the interface region.

57. The method of claim 55 or 56, wherein the chemical modification is replacing a hydrogen atom with a deuterium atom.

58. The method of claim 55 or 56, wherein the chemical modification is an introduction of an atom selected from the group consisting of a paramagnetic atom and a quadrupolar atom.

59. A method for identifying an atom of a common ligand that is proximal to an interface region of an enzyme;

wherein the enzyme binds a common ligand (CL) at a common ligand site (CL site) and binds a specificity ligand (SL) at an adjacent specificity ligand site (SL site);

wherein an interface region is defined as the atoms of the enzyme between the CL site and SL site, and atoms of an SL if bound to the enzyme;

wherein the enzyme catalyzes a reaction involving the SL and a reactive atom of the CL;

wherein a CL reactive region is defined as the reactive atom of the CL and CL atoms immediately adjacent to the reactive atom or CL atoms immediately adjacent to the SL;

and wherein an atom of the interface region has been identified;

comprising the steps of
  (1) binding a CL to the CL site of said enzyme;
  (2) irradiating the nucleus of the identified atom of the interface region; and
  (3) identifying in a multidimensional NMR experiment, an NMR cross-peak corresponding to a nucleus of the CL that is perturbed by the irradiation of the interface nucleus, thereby identifying an atom of the CL that is proximal to the interface region.

60. A method for identifying an atom of a common ligand that is proximal to an interface region of an enzyme;

wherein the enzyme can bind a common ligand (CL) at a common ligand site (CL site) and can bind a specificity ligand (SL) at an adjacent specificity ligand site (SL site);

wherein an interface region is defined as the atoms of the enzyme between the CL site and SL site, and atoms of an SL, if bound to the enzyme;

wherein the enzyme can catalyze a reaction involving the SL and a reactive atom of the CL; and wherein a CL reactive region is defined as the reactive atom of the CL and CL atoms immediately adjacent to the reactive atom or CL atoms immediately adjacent to the SL;

and wherein an atom of the interface region has been identified;

comprising the steps of
  (1) binding a CL to the CL site of said enzyme, and then performing a multidimensional NMR experiment;
  (2) binding a CL to the CL site of a chemically modified enzyme, wherein the modification is isotopic labeling at the atom of the interface region that has been identified, and then repeating the same NMR experiment;

(3) comparing the spectra from steps (1) and (2) to identify an NMR cross-peak corresponding to a nucleus that is affected by the chemical modification, thereby identifying an atom of the CL that is proximal to the interface region.

61. A method for identifying an atom of a specificity ligand mimic that is proximal to an interface region of an enzyme;

wherein the enzyme can bind a specificity ligand (SL) or a specificity ligand mimic (SL mimic) at a specificity ligand site (SL site) and can bind a common ligand (CL) at an adjacent common ligand site (CL site);

wherein an interface region is defined as the atoms of the enzyme between the SL site and CL site, and atoms of a CL, if bound to the enzyme;

wherein the enzyme can catalyze a reaction involving the CL and a reactive atom of the SL; and wherein a SL reactive region his defined as the reactive atom of the SL and SL atom immediately adjacent to the reactive atom or SL atoms immediately adjacent to the CL;

and wherein an atom of the interface region has been identified;

comprising the steps of
(1) binding a SL mimic to the SL site of said enzyme;
(2) irradiating the nucleus oft the identified atom of the interface region; and
(3) identifying in a multidimensional NMR experiment, an NMR cross-peak corresponding to a nucleus of the SL mimic that is perturbed by the irradiation of the interface nucleus, thereby identifying an atom of the SL mimic that is proximal to the interface region.

62. A method for identifying an atom of a specificity ligand mimic that is proximal to an interface region of an enzyme;

wherein the enzyme can bind a specificity ligand (SL) or a specificity ligand mimic (SL mimic) at a specificity ligand site (SL site) and can bind a common ligand (CL) at an adjacent common ligand site (CL site);

wherein an interface region is defined as the atoms of the enzyme between the SL site and CL site, and atoms of a CL, if bound to the enzyme;

wherein the enzyme can catalyze a reaction involving the CL and a reactive atom of the SL; and wherein a SL reactive region is defined as the reactive atom of the SL and SL atoms immediately adjacent to the reactive atom or SL atoms immediately adjacent to the CL;

and wherein an atom of thy interface region has been identified;

comprising the steps of
(1) binding a SL mimic to the SL site of said enzyme, and then performing a multidimensional NMR experiment;
(2) binding a SL mimic to the SL site of a chemically modified enzyme, wherein the modification is isotopic labeling at the atom of the interface region that has been identified, and then repeating the same NMR experiment;
(3) comparing the spectra from steps (1) and (2) to identify an NMR cross-peak corresponding to a nucleus that is affected by the chemical modification, thereby identifying an atom of the SL mimic that is proximal to the interface region.

* * * * *

UNITED STATES PATENT AND TRADEMARK OFFICE
CERTIFICATE OF CORRECTION

PATENT NO. : 6,620,589 B1
DATED : September 16, 2003
INVENTOR(S) : Sem et al.

It is certified that error appears in the above-identified patent and that said Letters Patent is hereby corrected as shown below:

Title page,
Item [73] ASSIGNEE, please delete "Traid", replace therefor with -- Triad --.
Item [56], References Cited, OTHER PUBLICATIONS, please delete *"sChem."*, replace therefor with -- *Chem.* --.
Item [57], ABSTRACT,
Line 10, please delete "us ed", replace therefor with -- used --.

Column 2,
Line 20, please delete "for Variation" and replace therefor with -- for variation --.

Column 3,
Line 29, please delete "thee" and replace therefor with -- the --.

Column 4,
Line 53, please delete "core'" and replace therefor with -- core- --.

Column 5,
Line 53, please delete "AND+" and replace therefor with -- NAD+ --.

Column 6,
Lines 7, 11, 13 and 28, please delete "AND+" and replace therefor with -- NAD+ --.

Column 7,
Lines 66 and 67, please delete "AND+" and replace therefor with -- NAD+ --.

Column 9,
Line 66, please delete "nucleu's" and replace therefor with -- nucleus --.

Column 10,
Line 36, please delete "corresponding. Larmor" and replace therefor with
-- corresponding Larmor --.

Column 12,
Line 26, please delete "large. proteins." and replace therefor with -- large proteins. --.

Column 14,
Line 8, please delete "uses. NMR" and replace therefor with -- uses NMR --.

UNITED STATES PATENT AND TRADEMARK OFFICE
CERTIFICATE OF CORRECTION

PATENT NO. : 6,620,589 B1
DATED : September 16, 2003
INVENTOR(S) : Sem et al.

It is certified that error appears in the above-identified patent and that said Letters Patent is hereby corrected as shown below:

Column 17,
Line 27, please delete "PGEX" and replace therefor with -- pGEX --.

Column 18,
Line 15, please delete "AND$^+$" and replace therefor with -- NAD$^+$ --.
Line 63, please delete "AND(P)H:quinone" and replace therefor with -- NAD(P)H:quinone --.

Column 21,
Line 47, please delete "37° C.", and replace therefor with -- 37° C --.

Column 26,
Line 42, please delete "geranyl-pyrophosphate." and replace therefor with -- geranyl-geranyl-pyrophosphate. --.
Line 48, please delete "site(&L :site)" and replace therefor with -- site (SL site) --.
Line 57, please delete "atoms in" and replace therefor with -- atoms --.

Column 27,
Line 12, please delete "SL mitt" and replace therefore with -- SL mimic --.

Column 29,
Line 59, please delete "identified" and replace therefor with -- modified --.

Column 31,
Line 22, please delete "region his" and replace therefor with -- region is --.
Line 23, please delete "SL atom" and replace therefor with -- SL atoms --.
Line 30, please delete "oft the" and replace therefor with -- of the --.

UNITED STATES PATENT AND TRADEMARK OFFICE
CERTIFICATE OF CORRECTION

PATENT NO. : 6,620,589 B1
DATED : September 16, 2003
INVENTOR(S) : Sem et al.

It is certified that error appears in the above-identified patent and that said Letters Patent is hereby corrected as shown below:

<u>Column 32,</u>
Line 19, please delete "of thy" and replace therefor with -- of the --.

Signed and Sealed this

Thirty-first Day of August, 2004

JON W. DUDAS
*Director of the United States Patent and Trademark Office*